US008157855B2

(12) United States Patent
Eidenschink et al.

(10) Patent No.: US 8,157,855 B2
(45) Date of Patent: Apr. 17, 2012

(54) DETACHABLE SEGMENT STENT

(75) Inventors: Tracee Eidenschink, Wayzata, MN (US); John Peckham, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 661 days.

(21) Appl. No.: 10/728,516

(22) Filed: Dec. 5, 2003

(65) Prior Publication Data
US 2005/0125051 A1    Jun. 9, 2005

(51) Int. Cl.
*A61F 2/06* (2006.01)
(52) U.S. Cl. .................................................. 623/1.15
(58) Field of Classification Search ............ 623/1.11, 623/1.12, 1.13–1.21
See application file for complete search history.

(56) References Cited

U.S. PATENT DOCUMENTS

| 5,091,205 A | 2/1992 | Fan ...................................... 427/2 |
| 5,122,136 A | 6/1992 | Guglielmi et al. ............... 606/32 |
| 5,423,829 A | 6/1995 | Pham et al. ..................... 606/108 |
| 5,591,197 A * | 1/1997 | Orth et al. ..................... 623/1.16 |
| 5,643,254 A | 7/1997 | Scheldrup et al. ............. 606/32 |
| 5,653,727 A | 8/1997 | Wiktor ............................ 606/195 |
| 5,755,770 A | 5/1998 | Ravenscroft ...................... 623/1 |
| 5,824,046 A | 10/1998 | Smith et al. ........................ 623/1 |
| 5,873,907 A * | 2/1999 | Frantzen ......................... 606/191 |
| 5,938,697 A * | 8/1999 | Killion et al. ................. 623/1.15 |
| 5,984,929 A | 11/1999 | Bashiri et al. ................. 606/108 |
| 6,039,757 A | 3/2000 | Edwards et al. ................... 623/1 |
| 6,059,779 A | 5/2000 | Mills ................................ 606/41 |
| 6,059,823 A | 5/2000 | Holman et al. .................... 623/1 |
| 6,077,260 A | 6/2000 | Wheelock et al. ............... 606/32 |
| 6,156,061 A | 12/2000 | Wallace et al. ................. 623/1.11 |
| 6,165,178 A | 12/2000 | Bashiri et al. ................. 606/108 |
| 6,168,618 B1 | 1/2001 | Frantzen ........................ 623/1.12 |
| 6,193,708 B1 | 2/2001 | Ken et al. ........................... 606/1 |
| 6,217,586 B1 | 4/2001 | Mackenzie .................... 606/108 |
| 6,221,099 B1 | 4/2001 | Andersen et al. ............. 623/1.15 |
| 6,231,597 B1 | 5/2001 | Deem et al. ................... 623/1.12 |
| 6,254,609 B1 | 7/2001 | Vrba et al. ..................... 606/108 |
| 6,258,117 B1 * | 7/2001 | Camrud et al. ............... 623/1.16 |
| 6,331,184 B1 | 12/2001 | Abrams ......................... 606/200 |
| 6,350,277 B1 | 2/2002 | Kocur ........................... 623/1.11 |
| 6,409,752 B1 | 6/2002 | Boatman et al. .............. 623/1.15 |
| 6,409,754 B1 * | 6/2002 | Smith et al. .................. 623/1.16 |
| 6,425,893 B1 | 7/2002 | Guglielmi ........................ 606/32 |
| 6,425,914 B1 | 7/2002 | Wallace et al. ............... 623/1.11 |
| 6,468,266 B1 | 10/2002 | Bashiri et al. ...................... 606/1 |
| 6,475,235 B1 | 11/2002 | Jayaraman ..................... 623/1.15 |
| 6,494,884 B2 | 12/2002 | Gifford, III et al. ........... 606/108 |

(Continued)

FOREIGN PATENT DOCUMENTS
WO    WO03063733    *  8/2003

*Primary Examiner* — Melanie Tyson
(74) *Attorney, Agent, or Firm* — Vidas, Arrett & Steinkraus, P.A.

(57) ABSTRACT

An inventive repositionable stent may comprise a plurality of adjacent serpentine bands connected to one another by at least one permanent connector strut and by at least one disengagable connector strut. The stent may self-expand within a bodily lumen to an intermediate deployment diameter, wherein the stent is constrained from further expansion by the at least one disengagable connector strut. The stent may be repositioned within the bodily lumen while in the intermediate deployment configuration. The disengagable connector strut may be disengaged via electrolytic detachment, whereupon the stent may expand to a full deployment diameter.

18 Claims, 34 Drawing Sheets

U.S. PATENT DOCUMENTS

| | | |
|---|---|---|
| 6,520,984 B1 | 2/2003 | Garrison et al. ............... 623/1.11 |
| 6,533,806 B1 | 3/2003 | Sullivan et al. ............... 623/1.11 |
| 6,562,067 B2 | 5/2003 | Mathis ............................ 623/1.16 |
| 6,579,308 B1 | 6/2003 | Jansen et al. .................. 623/1.15 |
| 6,585,757 B1 | 7/2003 | Callol ............................ 623/1.16 |
| 6,607,539 B1 | 8/2003 | Hayashi et al. ............... 606/108 |
| 6,613,077 B2* | 9/2003 | Gilligan et al. ............... 623/1.12 |
| 6,620,152 B2 | 9/2003 | Guglielmi ........................ 606/1 |
| 7,029,492 B1* | 4/2006 | Mitsudou et al. .............. 623/1.15 |
| 7,137,993 B2* | 11/2006 | Acosta et al. .................. 623/1.11 |
| 2002/0038132 A1 | 3/2002 | Abrams ........................... 606/200 |
| 2002/0107560 A1* | 8/2002 | Richter ........................... 623/1.11 |
| 2002/0111671 A1 | 8/2002 | Stenzel ........................... 623/1.16 |
| 2002/0188341 A1 | 12/2002 | Elliott ............................. 623/1.1 |
| 2002/0188347 A1 | 12/2002 | Mathis ............................ 623/1.19 |
| 2003/0014073 A1 | 1/2003 | Bashiri et al. .................. 606/200 |
| 2003/0045923 A1* | 3/2003 | Bashiri ............................ 623/1.12 |
| 2003/0135266 A1 | 7/2003 | Chew et al. .................... 623/1.16 |
| 2003/0144725 A1 | 7/2003 | Lombardi ...................... 623/1.13 |
| 2003/0199965 A1 | 10/2003 | Jansen et al. .................. 623/1.11 |
| 2004/0002752 A1* | 1/2004 | Griffin et al. .................. 623/1.15 |
| 2004/0093061 A1* | 5/2004 | Acosta et al. .................. 623/1.11 |

* cited by examiner

DETACHABLE SEGMENT STENT

BACKGROUND OF THE INVENTION

A stent is an elongated device used to support an intraluminal wall. A stent may be used, for example, to support a vessel or to treat a vascular aneurysm by removing the pressure on a weakened part of an artery so as to reduce the risk of rupture. Typically, a stent is implanted in a blood vessel at the site of a stenosis or aneurysm endoluminally, i.e. by so-called "minimally invasive techniques" in which the stent in a radially compressed configuration is delivered by a deployment system or "introducer" to the site where it is required. The introducer may enter the body through the patient's skin, or by a "cut down" technique in which the entry blood vessel is exposed by minor surgical means. When the introducer has been threaded into the body lumen to the prosthesis deployment location, the introducer is manipulated to cause the stent to be deployed and the stent allowed to expand or caused to expand at the deployment location, and the introducer is withdrawn. Stent expansion may be effected by a variety of mechanisms, including spring elasticity, balloon expansion, or by the self-expansion of a thermally or stress-induced return of a memory material to a pre-conditioned expanded configuration.

In the case of a self-expanding stent, the stent will generally self-expand to a full deployment diameter upon retraction of a constraining sheath. Thus, a self-expanding stent is desirably placed precisely at the intended deployment location as the sheath is retracted. Further, because resheathing is generally necessary for repositioning of a self-expanding stent, self-expanding stents generally utilize a closed-cell design, rather than an open cell design, to facilitate resheathing.

It would be desirable for a self-expanding stent to be repositionable within a bodily lumen after an initial partial self-expansion has been achieved.

It would be desirable to provide a resheathable self-expanding stent of open-cell design.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In one embodiment, an inventive stent comprises a plurality of serpentine bands, the adjacent serpentine bands being connected to one another by at least one permanent connector strut and by at least one disengagable connector strut. The disengagable connector strut may be disengaged by electrolytic detachment.

In another embodiment, an inventive stent comprises a cylindrical metal framework having a plurality of cells. The framework may comprise a first serpentine band, a second serpentine band, a permanent connector strut connecting the first serpentine to the second serpentine band, and a disengagable connector strut connecting the first serpentine to the second serpentine band. The disengagable connector strut may be disengaged by electrolytic detachment. Desirably, the number of cells may decrease upon disengagement of said disengagable connector strut, and the mass of the metal framework may decrease upon disengagement of said disengagable connector strut.

In another embodiment, an inventive stent comprises a cylindrical framework having a diameter, a first end and a second end. The framework may have a plurality of cells. A wire having a first end and a second end may be woven between at least two cells. Desirably, the first end of the wire may extend beyond an end of the framework. Desirably, the diameter of the cylindrical framework my be controlled by adjusting the tension of the wire.

In another embodiment, an inventive medical device comprises a delivery catheter, an implantable medical device arranged about the catheter, an inner sheath and an outer sheath. Desirably the inner sheath may be arranged about at least a portion of the implantable medical device and capable of expanding to a first maximum diameter. Desirably, the outer sheath may have a maximum diameter and be arranged about least a portion of the implantable medical device and about least a portion of the inner sheath. Desirably, the first maximum diameter of the inner sheath is greater than the maximum diameter of the outer sheath.

In another embodiment, an inventive stent comprises a proximal serpentine band, a distal serpentine band, at least one permanent connector strut and at least one cantilevered support member. Desirably, the cantilevered support member may have a first end coupled to the proximal serpentine band and a free second end. The second end may overlap the distal serpentine band. Desirably, the cantilevered support member is arranged to transmit a diameter-reducing force to the distal serpentine band.

In another embodiment, an inventive medical device delivery system comprises a stent and a delivery shaft, the stent being attached to the delivery shaft via an electrolytically detachable member.

In another embodiment, an inventive stent comprises a proximal serpentine band and a distal serpentine band. At least one permanent connector strut may connect the proximal serpentine band to the distal serpentine band. At least one floating connector strut may connect the proximal serpentine band to the distal serpentine band. A floating connector strut may include an interior loop. A portion of the proximal serpentine band may be contained within the interior loop.

These and other embodiments which characterize the invention are pointed out with particularity in the claims annexed hereto and forming a part hereof. However, for a better understanding of the invention, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

Figure 31:
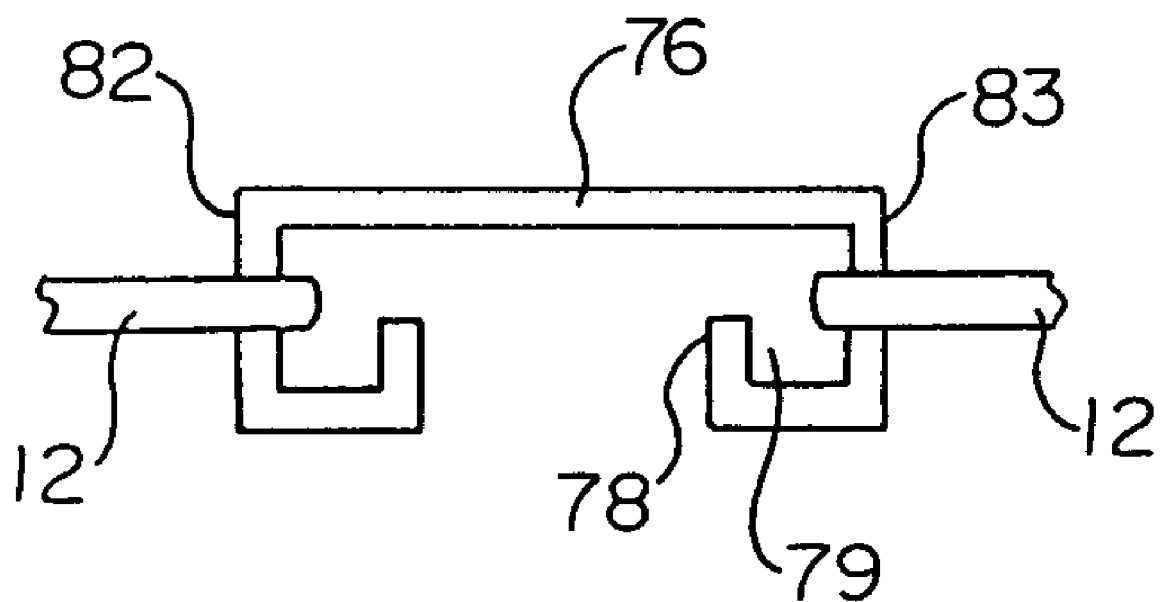
Figure 32:
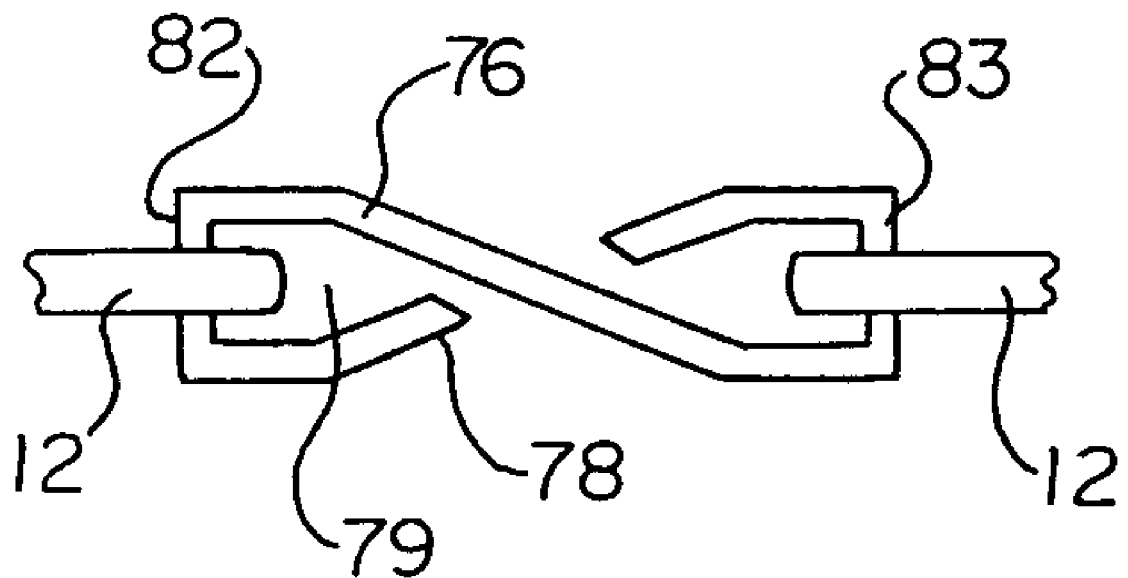
Figure 33:
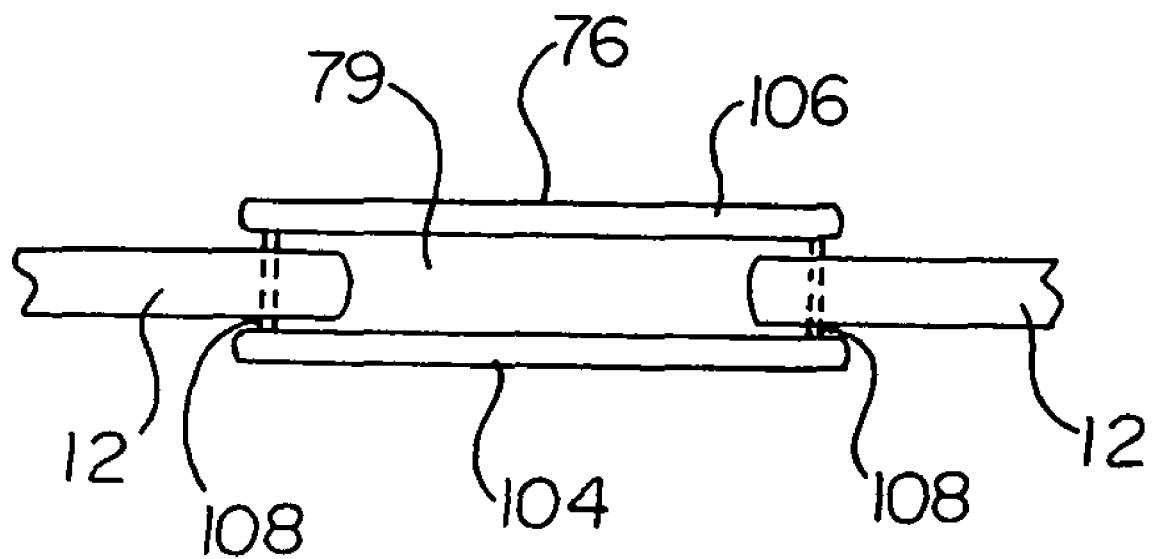
Figure 34:
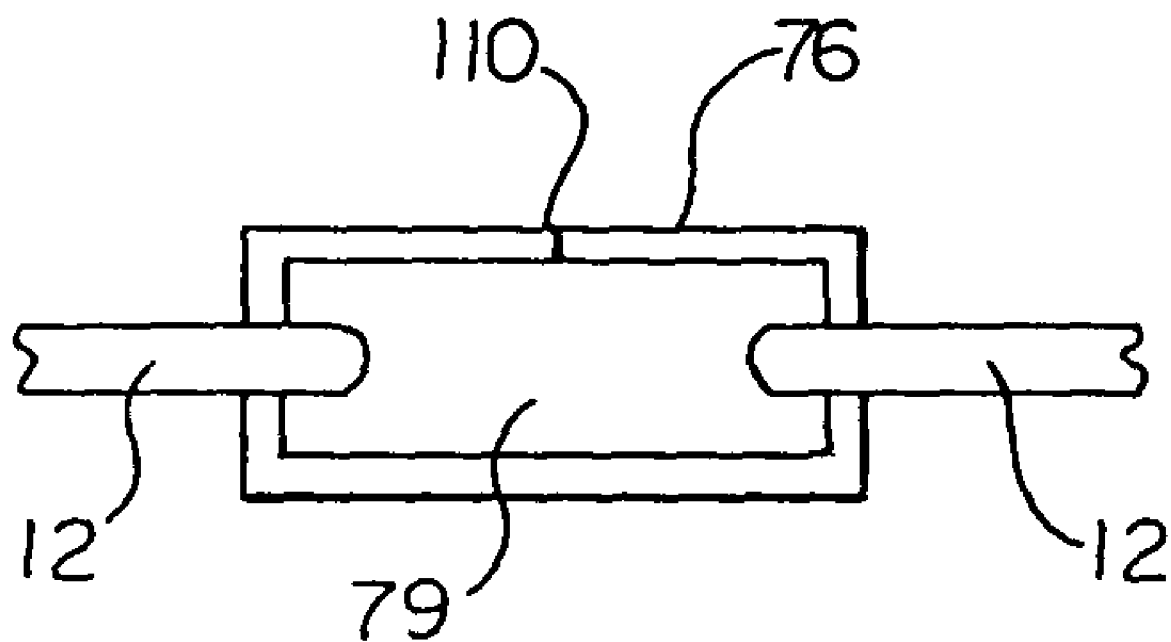

FIG. 31 shows an embodiment of a floating connector strut.
FIG. 32 shows an embodiment of a floating connector strut.
FIG. 33 shows an embodiment of a floating connector strut.
FIG. 34 shows an embodiment of a floating connector strut.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
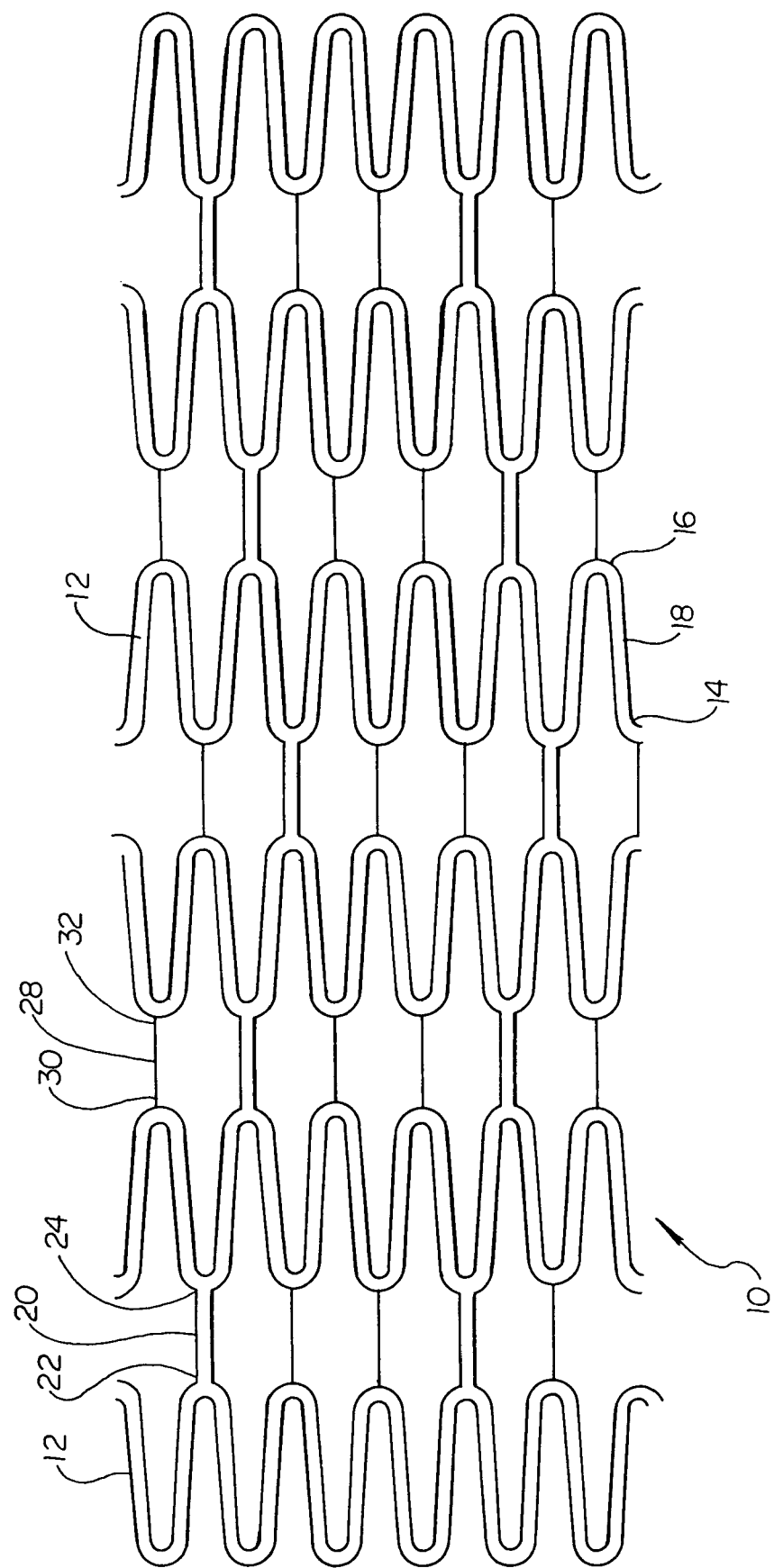
FIG. 1 shows a flat pattern for an embodiment of an inventive stent.
Figure 2:
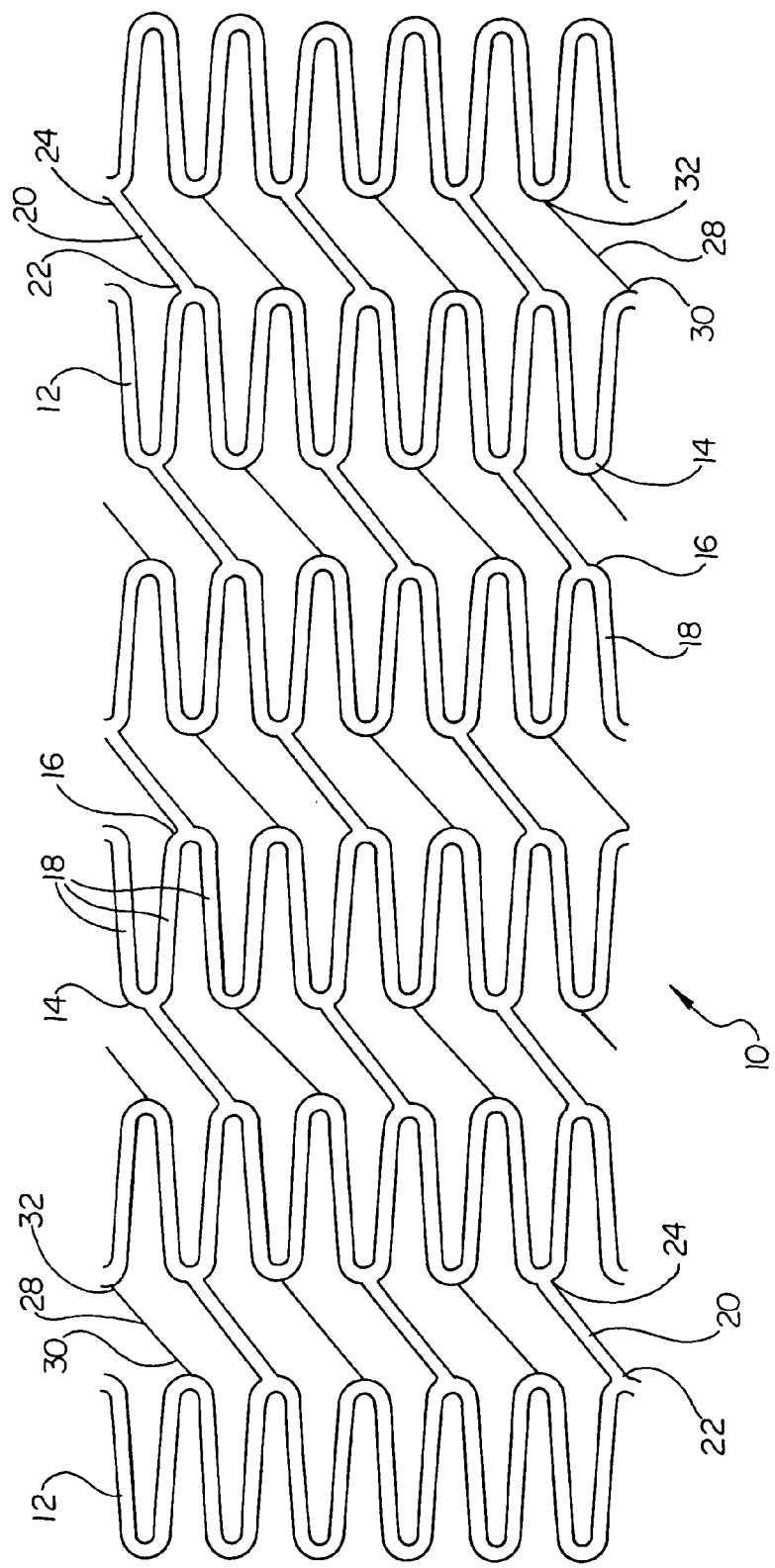
FIG. 2 shows a flat pattern for another embodiment of an inventive stent.

FIGS. 1 and 2 depict examples of flat patterns for inventive stents 10. In one embodiment, an inventive repositionable stent 10 comprises a plurality of serpentine bands 12. The serpentine bands 12 may be arranged such that each serpentine band 12 traverses a circumference of a portion of the inventive stent 10. In some embodiments, each serpentine band 12 may comprise a plurality of straight portions 18, each straight portion 18 being connected at one end to an adjacent straight portion 18 by a peak 14, and being connected at the other end to another adjacent straight portion 18 by a valley 16.

Serpentine bands 12 may be arranged adjacent to one another along the longitudinal axis of the stent 10. Adjacent serpentine bands 12 may be connected to one another by at least one permanent connector strut 20. A permanent connector strut 20 may have a proximal end 22 and a distal end 24, and may be connected at the proximal end 22 to a serpentine band 12, and connected at the distal end 24 to another serpentine band 12. In some embodiments, a permanent connector strut 20 proximal end 22 may connect to a valley 16 of one serpentine band 12, and the permanent connector strut 20 distal end 24 may connect to a peak 14 of another serpentine band 12.

Adjacent serpentine bands 12 may further be connected to one another by at least one detachable or disengagable connector strut 28. A disengagable connector strut 28 may have a proximal end 30 and a distal end 32, and may be connected at the proximal end 30 to a serpentine band 12, and connected at the distal end 32 to another serpentine band 24. In some embodiments, a disengagable connector strut 28 proximal end 30 may connect to a valley 16 of one serpentine band 12, and the disengagable connector strut 28 distal end 32 may connect to a peak 14 of another serpentine band 12.

In some embodiments, a stent 10 comprises more disengagable connector struts 28 than permanent connector struts 20.

Disengagable connector struts 28 are designed to have a detaching or disengaging mechanism. Upon disengagement, the disengagable connector strut 28 will generally cease to transmit forces between the adjacent serpentine bands 12 to which it was originally attached.

Desirably a disengagable connector strut 28 will allow for the stent 10 to be repositionable after the stent 10 is initially deployed. Thus, after a sheath is removed and the stent 10 is allowed to self-expand to a diameter greater than the unexpanded delivery diameter, the disengagable connector struts 28 may allow for the stent 10 to be repositioned prior to disengaging the disengagable connector struts 28.

In some embodiments, a disengagable connector strut 28 may detach from at least one of the serpentine bands 12 to which it was originally attached. Thus, a disengagable connector strut 28 proximal end 30 may disconnect from a valley 16 to which it is attached. Likewise, a disengagable connector strut 28 distal end 32 may disconnect from a peak 14 to which it is attached.

In some embodiments, a disengagable connector strut 28 may sever into at least two portions, and each portion may or may not remain attached to a respective serpentine band 12.

In some embodiments, disengagable connector struts 28 may confine the stent 10 to an intermediate deployment diameter. An intermediate deployment diameter is less than the full and final deployment diameter of the stent 10. When disengagable connector struts 28 confine the stent 10 to an intermediate deployment diameter, the stent 10 is desirably capable of being repositioned within a bodily lumen at the intermediate deployment diameter. Upon disengagement of the disengagable connector struts 28, the stent 10 may expand to the full deployment diameter.

In some embodiments, the disengagable connector struts 28 may be detached via electrolytic detachment, such as by the detachment mechanisms disclosed in U.S. Pat. Nos. 5,122,136, 5,423,829, 5,643,254 and U.S. Pat. No. 6,059,779, the entire disclosures of which are incorporated herein by reference.

Generally, an electrical current may flow through the disengagable connector struts 28 and be dispersed into a bodily fluid such as blood contained within a bodily lumen. As the current flows, portions of the disengagable connector struts 28 may experience electrolytic corrosion. Upon the electrolytic corrosion of an appropriate amount of a disengagable connector strut 28, the disengagable connector strut 28 will disengage.

In some embodiments, disengagement may occur when electrolytic corrosion has penetrated a full cross-section of a portion of a disengagable connector strut 28.

In some embodiments, such as when a stent 10 is a self-expanding stent, disengagement may occur as a combination of electrolytic corrosion and mechanical deformation. Namely, a disengagable connector strut 28 may experience electrolytic corrosion to a point where the mechanical self-expanding forces of the stent 10 provide enough of a stress upon the disengagable connector strut 28 to strain and fracture or rupture the disengagable connector strut 28, thereby achieving disengagement.

Disengagable connector struts 28 may be affixed to the stent 10 via the use of adhesives, laser welding techniques, other welding or brazing techniques, swaging and the like. In some embodiments, the disengagable connector struts 28 may be formed from the same material as the rest of the stent 10, such as when a stent is laser cut from a tube of material.

In some embodiments, the disengagable connector struts 28 may be in electrical communication with the remainder of the stent 10. Desirably, the disengagable connector struts 28 have a higher corrosion potential than the remainder of stent 10. Thus, if a current is applied to the entire stent 10, the disengagable connector struts 28 will corrode faster than other portions of the stent 10 due to electrolytic corrosion. Desirably, the disengagable connector struts 28 will achieve detachment before a noticeable corrosion of other portions of the stent 10.

Any suitable material may be selected for the disengagable connector struts 28. Materials utilized for the disengagable connector struts 28 may include but are not necessarily limited to magnesium, zinc, aluminum, mild steel, low alloy steel, stainless steel, Nitinol, iron and/or cobalt chromium alloys such as elgiloy. Desirably, the disengagable connector struts 28 will be made of mild steel, low alloy steel, zinc, aluminum, and magnesium.

The range of materials available for functioning as the disengagable connector struts 28 is quite large and is not limited to the materials identified within the specification. It is anticipated that any suitable metallic material may be utilized as the electrolytically disengagable connector struts 28, provided that the material selected will allow for proper detachment of the disengagable connector struts 28 without a substantial degradation of the other portions of the stent 10.

Figure 3:
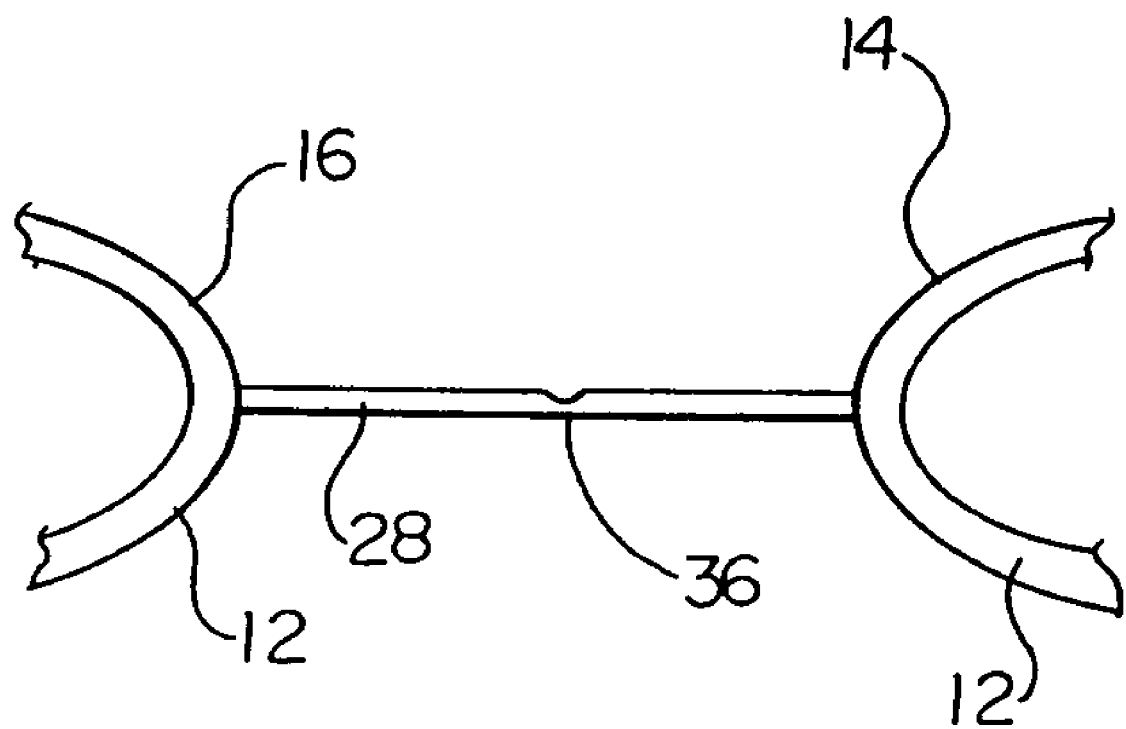
FIG. 3 shows an embodiment of a disengagable connector strut.
Figure 4:
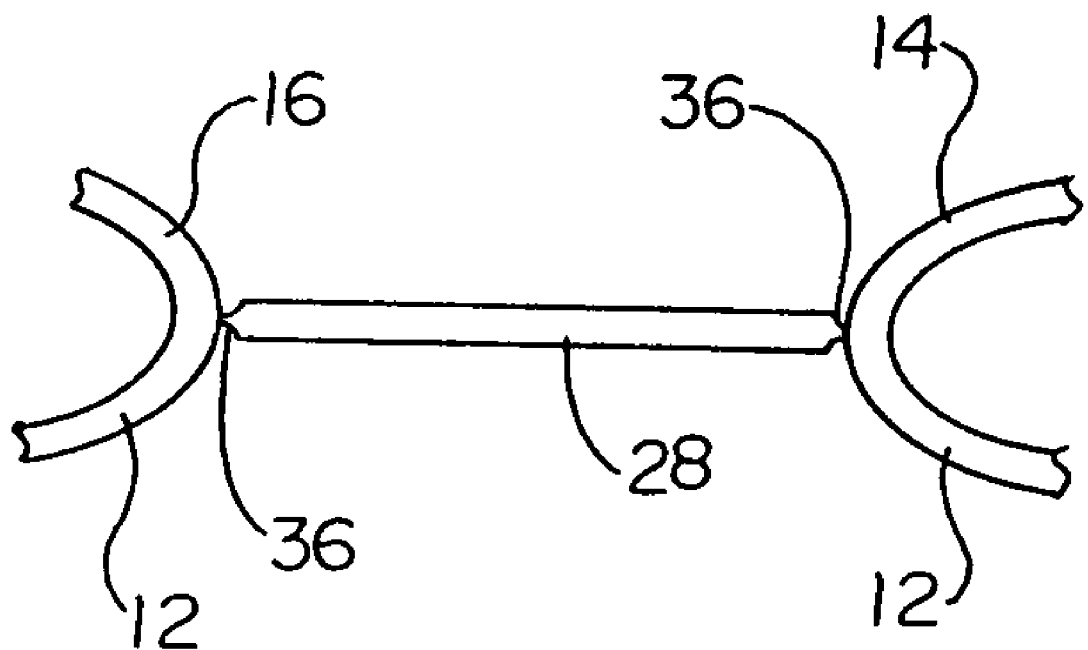
FIG. 4 shows another embodiment of a disengagable connector strut.

The disengagable connector struts 28 may generally be any size as desired for use in a medical procedure, and may include a reduced or necked portion 36 as shown in FIGS. 3 and 4. Generally, a necked portion 36 will serve as a detachment point. Disengagable connector struts 28 may be cylindrical in shape and cross-section. The disengagable connector struts 28 may also be provided in other geometric shape as desired, such as rectangular, trapezoidal, triangular, and the like. The size and shape of the disengagable connector struts 28 may vary considerably dependent upon the size and material of the stent 10 being used, and by the exact embodiment and method being used to accomplish electrolytic detachment of the disengagable connector struts 28.

Exposure of electrical current to the disengagable connector struts 28 initiates corrosion/deterioration of the disengagable connector struts 28. The material selected for the disengagable connector struts 28 desirably corrodes more rapidly due to a higher corrosion potential than materials selected for the rest of the stent 10. However, when the disengagable connector struts 28 are made from the same material as the rest of the stent 10, the disengagable connector struts 28 are desirably sized and shaped to allow for a rapid electrolytic detachment.

In some embodiments, a disengagable connector strut 28 may act as a fuse portion. Thus, detachment may be accomplished by melting a portion of the disengagable connector strut 28. Generally, a melting detachment will occur at a necked portion 36. Desirably, the disengagable connector struts 28, and especially the necked portion 36, will have a substantially smaller cross-sectional area than other portions of the stent 10 such that detachment may occur without any consequential damage to other portions of the stent 10.

When inserting and implanting a stent 10 within a bodily lumen, and detaching the disengagable connector struts 28 using electrolytic detachment methods, the stent 10 is generally delivered to a deployment site using a delivery catheter. When the stent 10 is at least partially self-expanding, a sheath is generally used to constrain the stent 10 upon the catheter as is known in the art. Upon arrival of the stent 10 at the deployment site, the sheath is removed and the stent 10 is allowed to expand.

Upon removal of a sheath, an inventive self-expanding stent 10 will generally self-expand to a partially expanded or intermediate deployment diameter. Desirably the disengagable connector struts 28 prevent expansion of the stent 10 beyond an intermediate deployment diameter. Desirably, the stent 10 may be easily repositioned within the bodily lumen when expanded to an intermediate deployment diameter.

An electrical current may then be applied to the disengagable connector struts 28 to facilitate detachment. Upon detachment of the disengagable connector struts 28, the stent 10 may expand to a full deployment diameter.

Figure 5:
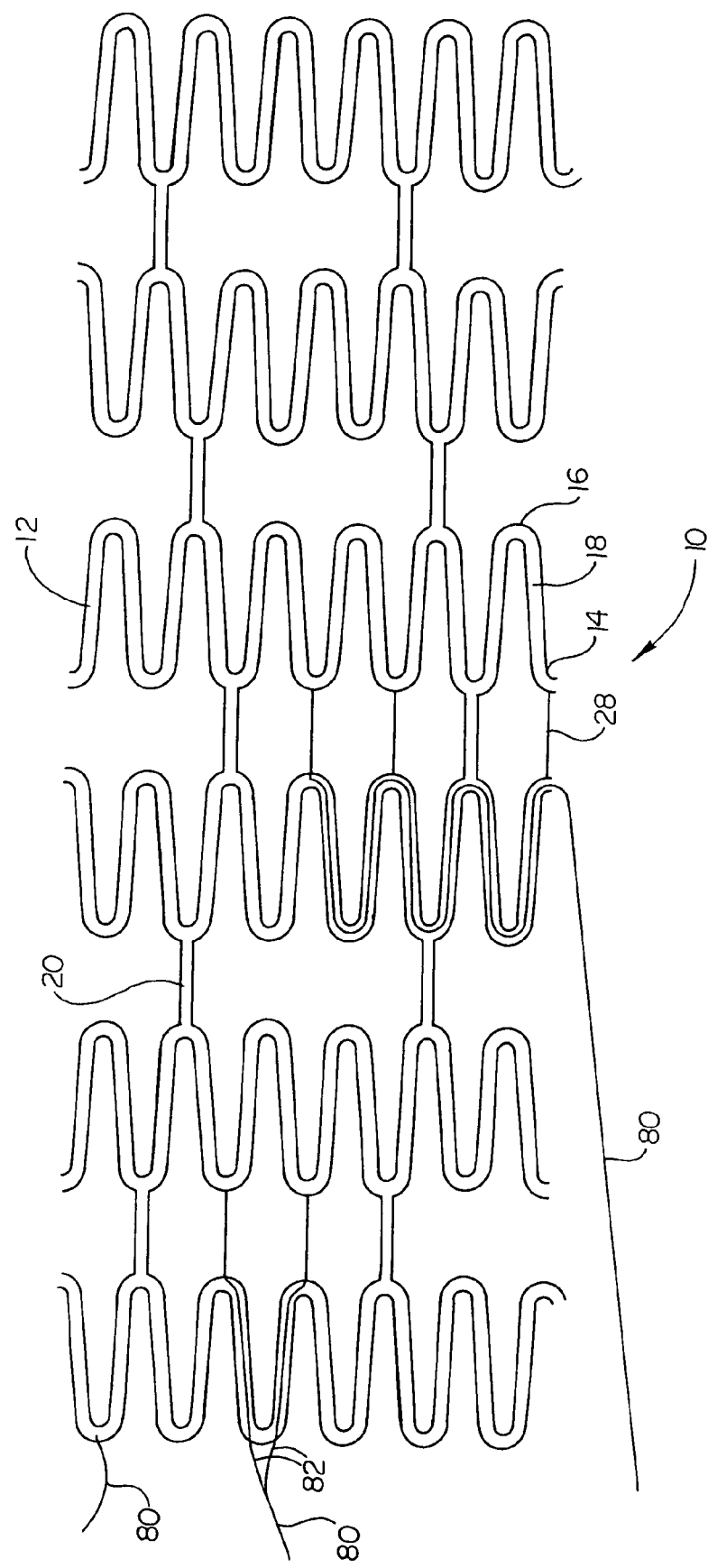
FIG. 5 shows features of other embodiments of an inventive stent.

As shown in FIG. 5, a stent 10 may include an electrical lead 80. In some embodiments, an electrical lead 80 may be mechanically and electrically coupled to a portion of the stent 10. An electrical lead 80 may extend proximally from the stent 10 along the length of a delivery catheter to outside the body of a patient. When a source of electrical potential is applied to the lead 80, an electrical current will flow through the stent 10 and the disengagable connector struts 28, thereby initiating detachment of each disengagable connector strut 28 and allowing the stent 10 to expand to the full deployment diameter. The material for the disengagable connector struts 28 and the size and cross-sectional area of the disengagable connector struts 28 should be selected to facilitate detachment of the disengagable connector struts 28 without a consequential degradation of other portions of the stent 10.

An electrical lead 80 may be designed to detach from the stent 10 via electrolytic detachment after all of the disengagable connector struts 28 have achieved a successful detachment. An electrical lead 80 may be designed to detach from the stent 10 when a predetermined tensile load is placed upon the lead 80.

In some embodiments, an electrical lead 80 may be electrically insulated from the stent 10, and may be electrically connected directly to the disengagable connector struts 28.

In some embodiments, a single electrical lead 80 may split into a plurality of branches 82 and may connect in parallel to a plurality of disengagable connector struts 28. For example, an electrical lead 80 may be connected in parallel to each disengagable connector strut 28 that spans between a first serpentine band 12 and a second serpentine band 12.

In some embodiments, multiple electrical leads 80 may be used.

In some embodiments, a separate electrical lead 80 may be provided for each disengagable connector strut 28.

Figure 6:
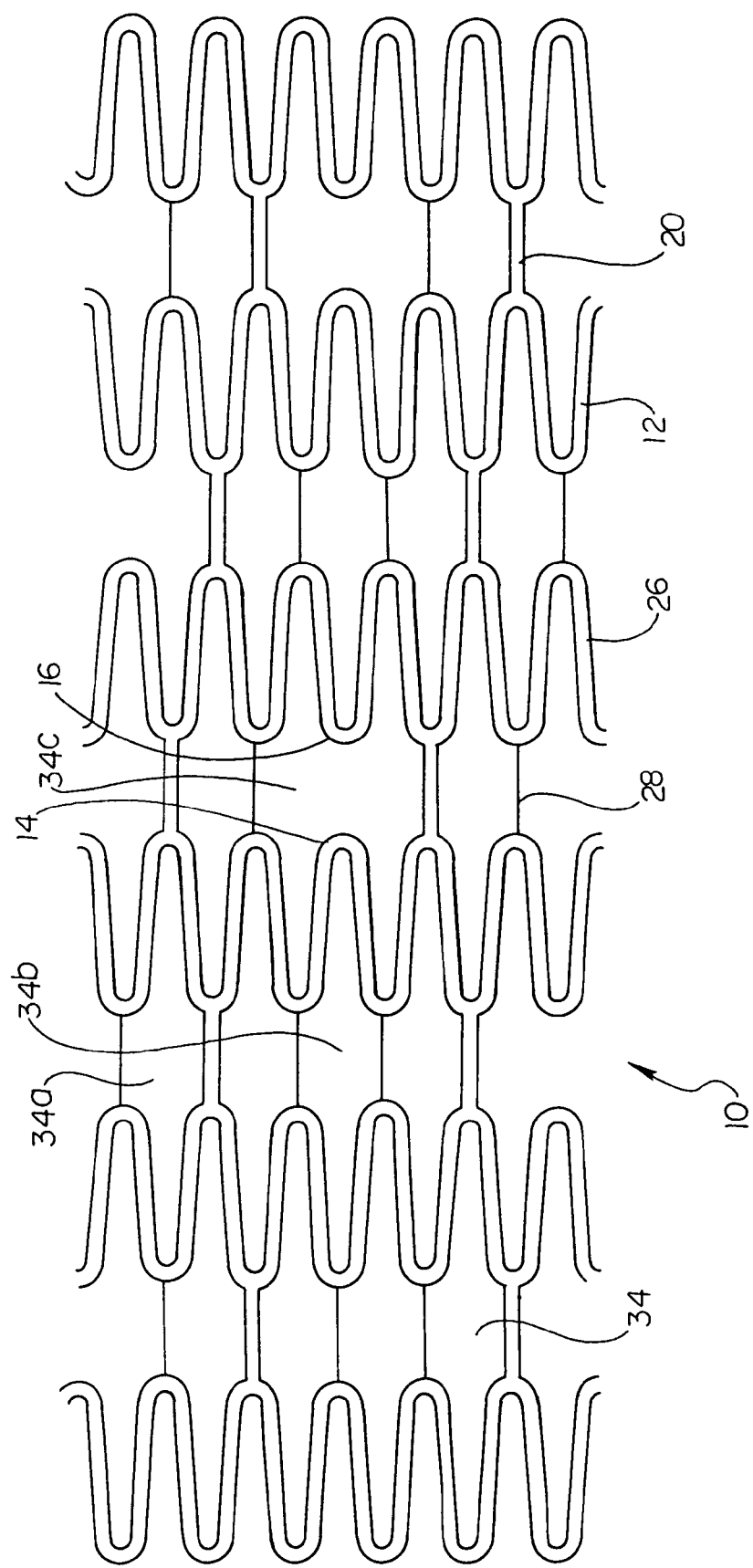
FIG. 6 shows a flat pattern for another embodiment of an inventive stent.

Referring to FIG. 6, in some embodiments, an inventive stent 10 may comprise a framework 26 having a plurality of openings or cells 34. The framework 26 may comprise serpentine bands 12, permanent connector struts 20, disengagable connector struts 28, and any other portions of the stent 10.

Generally, a cell 34 is an open area in the wall of a stent 10 bounded by framework 26 elements. Desirably, the framework 26 elements are continuous about the perimeter of a cell 34.

FIG. 6 shows a few examples of possible cell 34 configurations. For example, a cell 34*a* may be bounded by a portion of a first serpentine band 12, a disengagable connector strut 28, a portion of a second serpentine band 12, and a permanent connector strut 20. A cell 34*b* may be bounded by a portion of a first serpentine band 12, a first disengagable connector strut 28, a portion of a second serpentine band 12, and a second disengagable connector strut 28. Cells 34 may include portions of serpentine bands 12 having multiple peaks 14 and valleys 16, as depicted by cell 34*c*.

Figure 7:
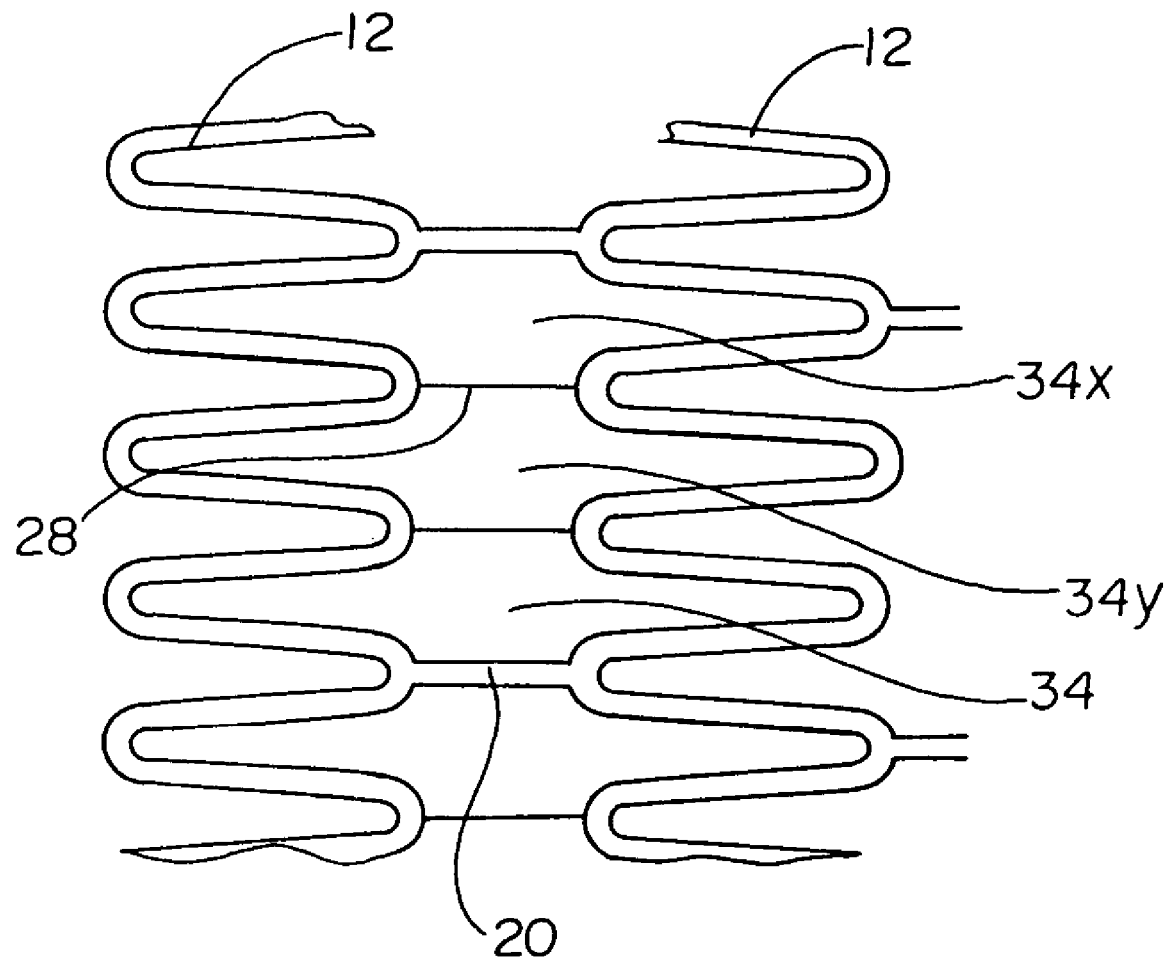
FIG. 7 shows a portion of an embodiment of an inventive stent.
Figure 8:
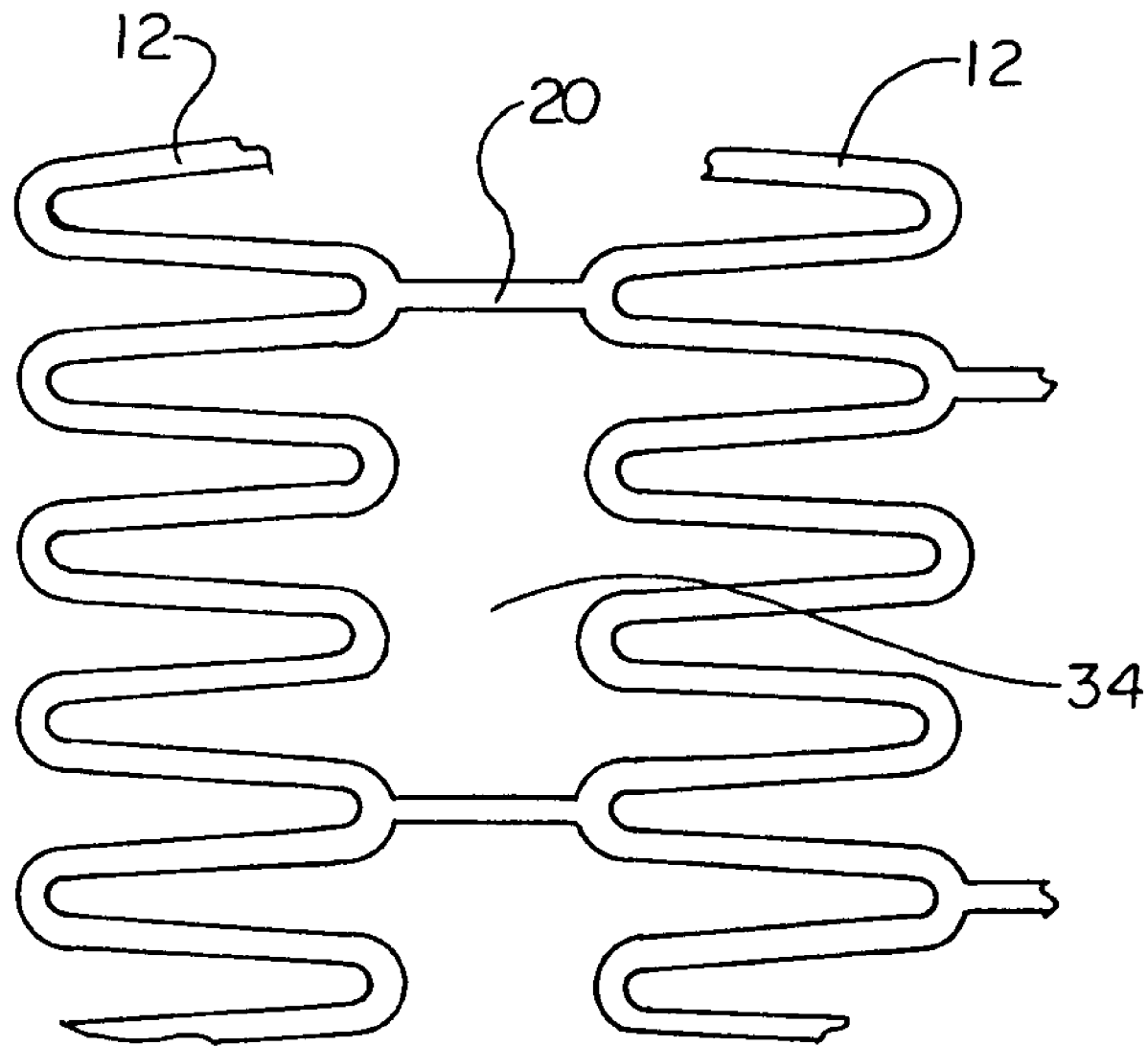
FIG. 8 shows a portion of an embodiment of an inventive stent.

An inventive stent 10 may include a predetermined number of cells 34. FIGS. 7 and 8 show a portion of an inventive stent 10 before and after detachment of the disengagable connector struts 28. Generally, before detachment of any disengagable connector struts 28, each disengagable connector strut 28 defines on one side of the strut 28 a portion of a first cell 34*x*, and defines on another side of the strut 28 a portion of a second, adjacent cell 34*y*.

Upon detachment of a disengagable connector strut 28, the cells 34*x*, 34*y* formerly defined by the disengagable connector strut 28 may combine to form a single, larger cell 34. In some embodiments, a plurality of cells 34 may combine to form a single cell 34 upon detachment of the disengagable connector struts 28. Thus, the total number of cells 34 in a stent 10 may decrease upon the detachment or disengagement of one or more disengagable connector struts 28.

Upon detachment of a disengagable connector strut 28, the mass of the framework 26 may decrease upon detachment of a disengagable connector strut 28.

In some embodiments, when all of the disengagable connector struts 28 in a stent 10 have been detached, all of the cells 34 of the stent 10 may be bounded by a portion of a first serpentine band 12, a first permanent connector strut 20, a portion of a second serpentine band 12, and a second permanent connector strut 20.

In some embodiments, disengagable connector struts 28 may allow for the complete resheathing of a partially unsheathed self-expanding stent.

Figure 9:
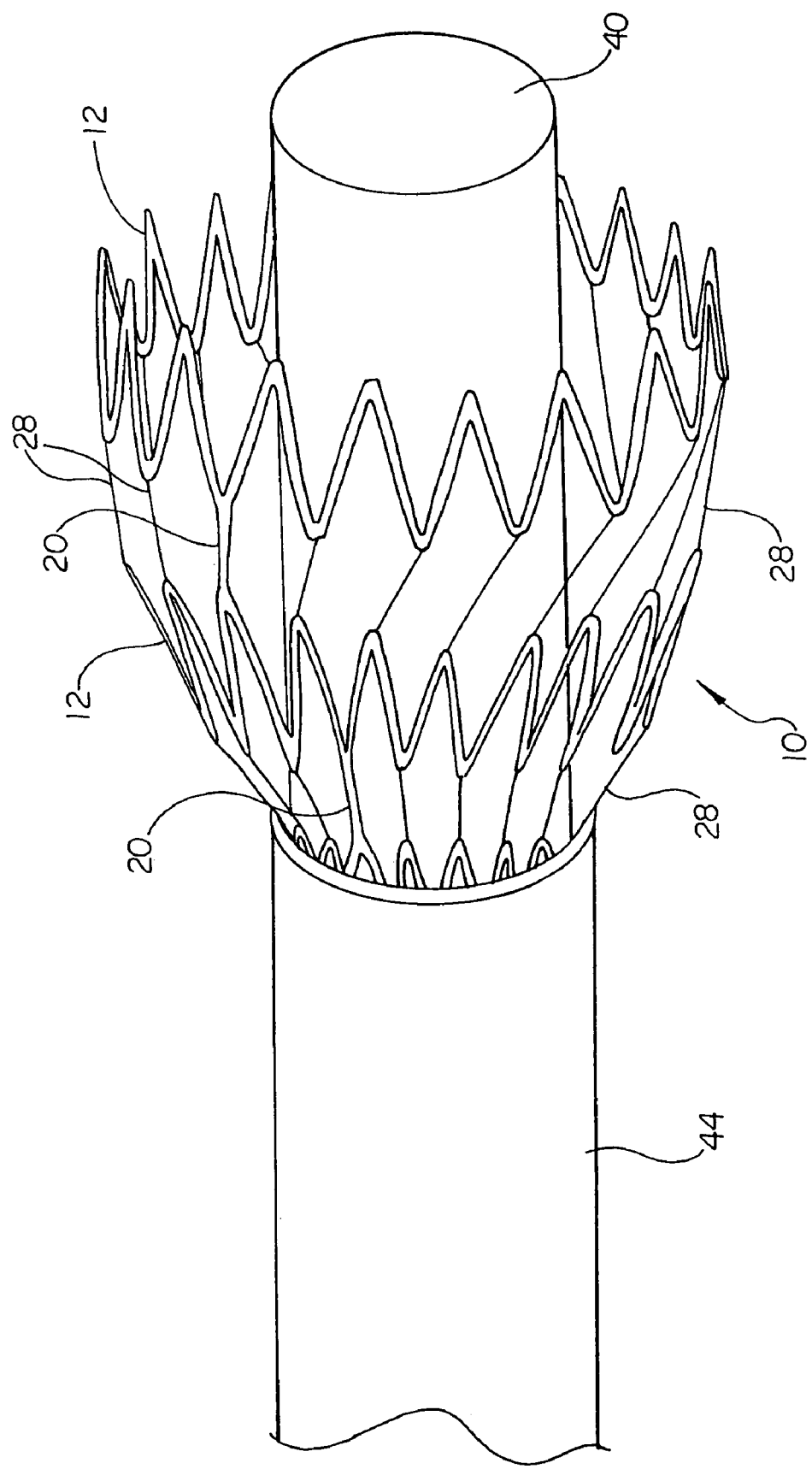
FIG. 9 shows an embodiment of an inventive stent disposed about a catheter with a sheath.
Figure 10:
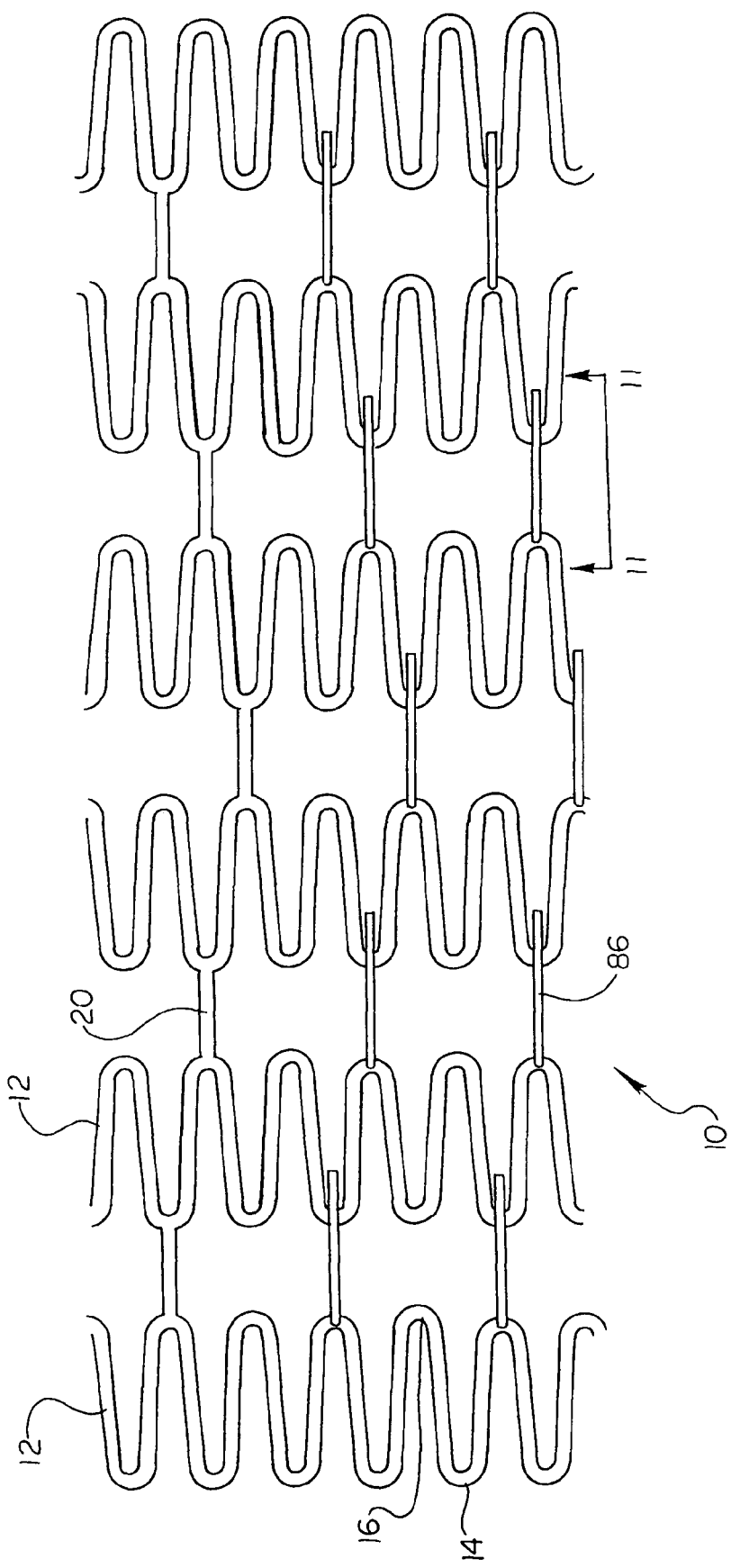
FIG. 10 shows another embodiment of an inventive stent.

FIG. 9 shows an embodiment of a self-expanding stent 10 having a plurality of serpentine bands 12, a permanent connector strut 20 connecting adjacent serpentine bands 12, and a plurality of disengagable connector struts 28 connecting adjacent serpentine bands 12. The stent 10 is arranged about a catheter 40, and a portion of the stent 10 is constrained by a sheath 44. Generally, to unsheath a self-expanding stent 10, the sheath 44 is moved proximally in relation to the stent 10 although other arrangements of a catheter may be provided such that the sheath is retracted in a distal direction. Desirably, the stent 10 is not fully unsheathed until proper placement with a bodily vessel is achieved.

When repositioning of the stent 10 is desired before the stent 10 has been fully unsheathed, the sheath 44 may be moved distally to again cover portions of the stent 10. Disengagable connector struts 28 may form a structural connection between adjacent serpentine bands 12, and may transmit constraining forces from the sheath 44 and portions of the stent 10 beneath the sheath 44 to serpentine bands 12 not yet covered by the sheath 44. As the sheath 44 moves distally, the disengagable connector struts 28 pull the distal serpentine bands 12 inward and allow the serpentine bands 12 to be reduced to the diameter of the sheath 44. Further, the presence of disengagable connector struts 28 may eliminate free valleys 16 that could snag the sheath 44. Thus, the stent 10 may be resheathed and repositioned within the bodily lumen.

Referring to FIGS. 10-13, in some embodiments, a repositionable stent 10 may comprise a plurality of serpentine bands 12, at least one permanent connector strut 20 connecting adjacent serpentine bands 12, and at least one cantilevered support member 86. A cantilevered support member 86 may comprise a force transmitting element capable of transmitting selected forces between adjacent serpentine bands 12. Desirably, a cantilevered support member 86 may transmit a constraining or diameter-reducing force from a first serpentine band 12 to an adjacent serpentine band 12.

A cantilevered support member 86 may be coupled at one end to a first serpentine band 12. The coupling may comprise a rigid connection 88. Cantilevered support members 86 may be affixed to the serpentine band 12 via the use of adhesives, laser welding techniques, other welding or brazing techniques, swaging or any other suitable methods. Desirably, the connection 88 may be near a valley 16 portion of the first serpentine band 12. The cantilevered support member 86 may extend distal to the first serpentine band 12 and overlap an adjacent serpentine band 12. The overlap may be near a peak 14 of the adjacent serpentine band 12. In some embodiments, a cantilevered support member 86 will only interact with the adjacent serpentine band 12 by applying a constraining force, such as a force in a radial direction toward the center of the stent 10. Thus, a cantilevered support member 86 may be arranged to allow adjacent serpentine bands 12 to move proximally or distally with respect to one another along the longitudinal axis of the stent 10.

Cantilevered support members 86 may include any cross-sectional shape. For example, the cross-section may be circular, rectangular, trapezoidal, ovular, or any other suitable shape.

Figure 11:
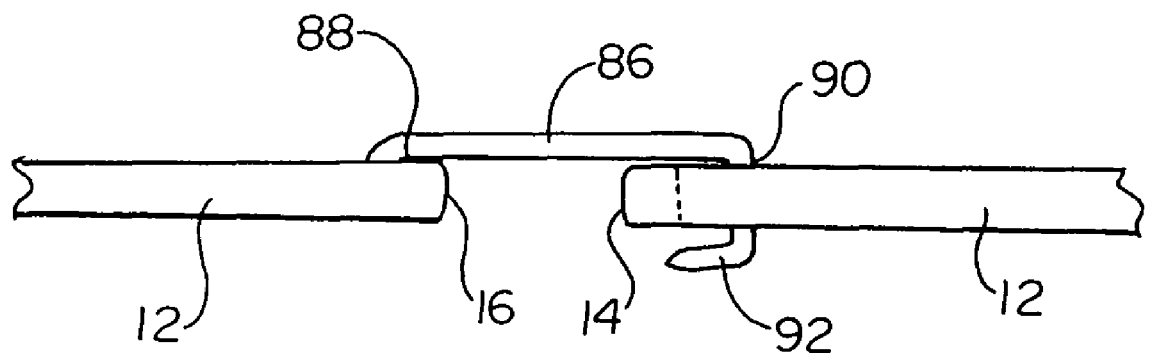
FIG. 11 shows an embodiment of a cantilevered support member taken along line 11-11 of FIG. 10.
Figure 12:
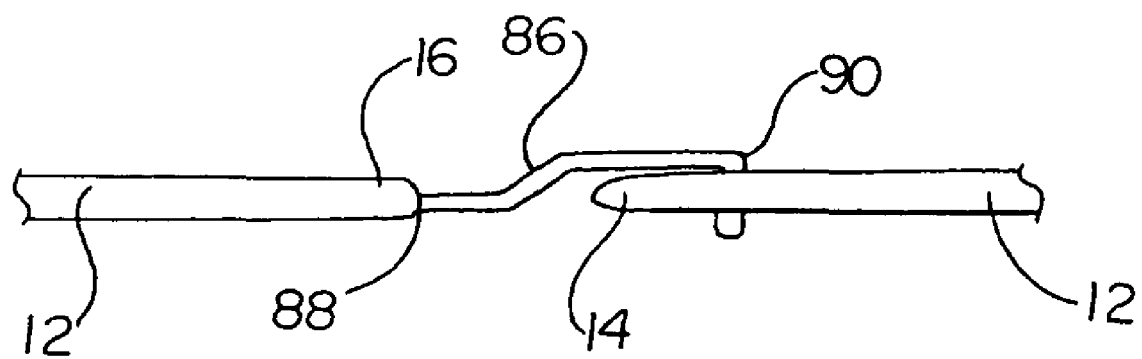
FIG. 12 shows another embodiment of a cantilevered support member.
Figure 13:
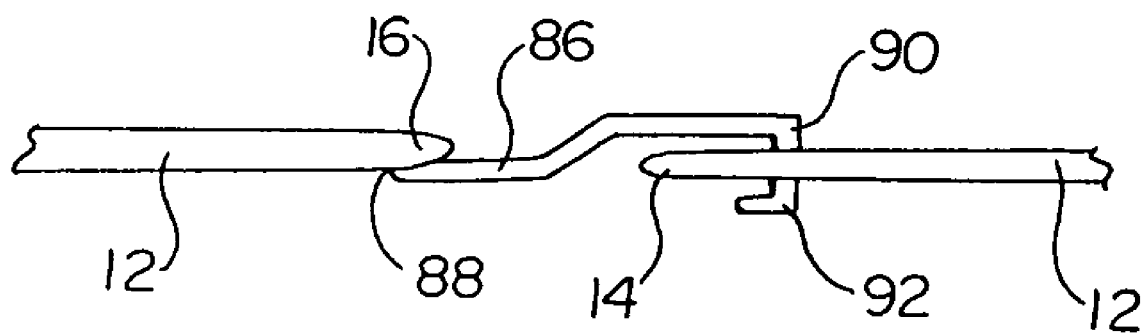
FIG. 13 shows another embodiment of a cantilevered support member.
Figure 14:
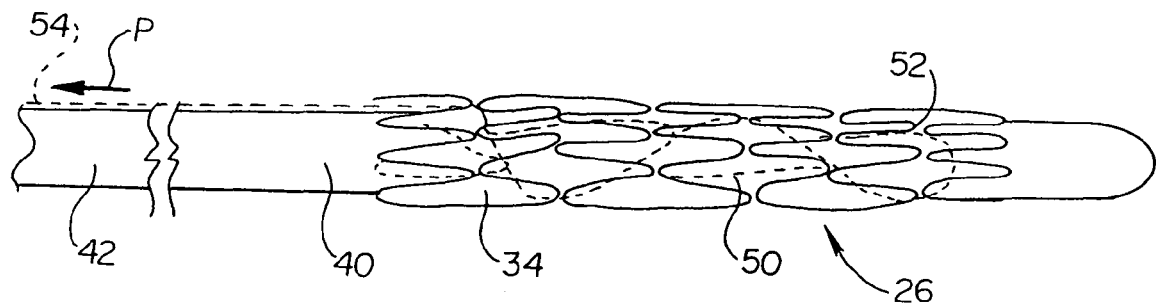
FIG. 14 shows an embodiment of an inventive stent having a restraining wire.
Figure 15:
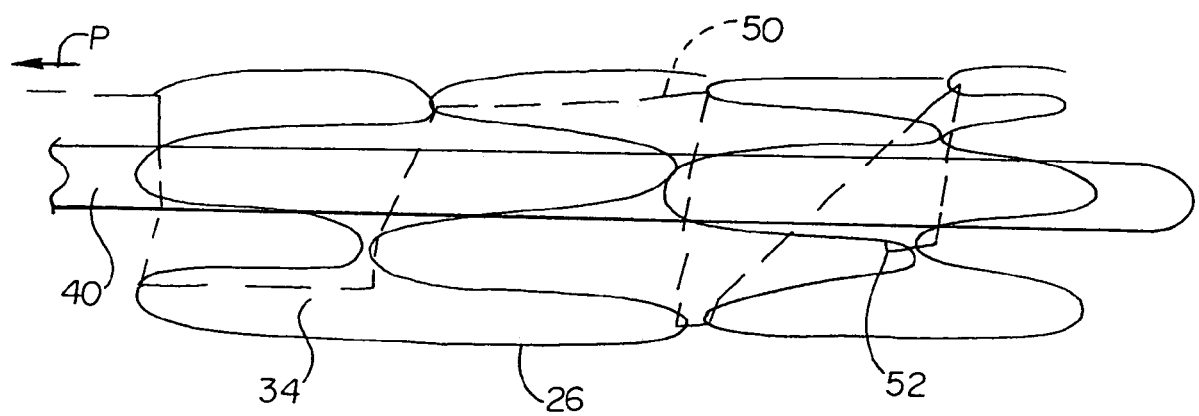
FIG. 15 shows an embodiment of an inventive stent having a restraining wire in a partially expanded configuration.

Cantilevered support members 86 may be coupled to a serpentine band 12 at any location of the serpentine band 12. Thus, the connection 88 may be arranged on the outer edge of the stent 10, as shown in FIG. 11. The connection may be on a side of a serpentine band 12, as shown in FIG. 12, or on the inner edge of the stent 10 as shown in FIG. 13. Further, the connection 88 may be placed anywhere along the serpentine band 12, and need not be limited to peaks 14 or valleys 16.

Similarly, a cantilevered support member 86 may overlap an adjacent serpentine band 12 anywhere along the adjacent serpentine band 12.

Cantilevered support members 86 may extend parallel to the longitudinal axis of the stent 10, or may extend at an angle. An angle may be desirable, for example, when the peaks 14 and valleys 16 of adjacent serpentine bands 12 are not aligned. Further, a cantilevered support member 86 may be straight or may be curved along at least a portion of its length, if not the entirety of its length.

Cantilevered support members 86 desirably allow a partially unsheathed self-expanding stent 10 to be resheathed. When a first serpentine band 12 is reduced in diameter, cantilevered support members 86 that are coupled to the first band 12 may transmit a constraining force to an adjacent serpentine band 12, thereby reducing the diameter of the adjacent band 12. Thus, a partially unsheathed self-expanding stent 10 having cantilevered support members 86 may be resheathed and repositioned within a bodily lumen.

Any number of cantilevered support members 86 may be used within a stent 10. Desirably, at least one cantilevered support member 86 may be placed between adjacent serpentine bands 12.

Desirably, under normal conditions for a deployed stent 10, a cantilevered support member 86 will allow the adjacent serpentine bands 12 to move laterally with respect to one another without interference.

As shown in FIGS. 11-13, in some embodiments, a cantilevered support member 86 may include a bent end portion 90. The bent end portion 90 may be angled or curved. The term 'bent' is not intended to be limited to any particular manufacturing process. A cantilevered support member 86 may also include a hook 91. A bent end portion 90 may engage the adjacent serpentine band 12 in the stent 10 longitudinal direction. A hook 91 may engage an adjacent serpentine band 12 in a stent 10 radial direction.

In connection with the length of the cantilevered support member 86, a curved end portion 90 may allow a cantilevered support member 86 to engage an adjacent serpentine band 12 to prevent the adjacent serpentine band 12 from laterally displacing more than a predetermined distance away from the first serpentine band 12. Thus, in some embodiments, a cantilevered support member 86 may be used to limit the distance between adjacent serpentine bands 12. Desirably, an appropriate length for each cantilevered support member 86 may be chosen depending upon the stent 10 and the desired distance between serpentine bands 12.

A curved or angled end portion 90 and a hook 91 may help to prevent the adjacent serpentine band 12 from moving away from the first serpentine band 12 a distance greater than the length of the cantilevered support member 86. Thus, a curved or angled end portion 90 and a hook 91 may help to prevent an adjacent serpentine band 12 from escaping the constraining forces of the cantilevered support member 86.

Referring to FIGS. 14-17, in another embodiment, an inventive repositionable stent 10 may comprise a substantially cylindrical framework 26 having a plurality of cells 34 and a constraining or restraining wire 50. In some embodiments, the substantially cylindrical framework 26 comprises a plurality of serpentine bands 12. The serpentine bands 12 may be arranged such that each serpentine band 12 traverses a circumference of a portion of the inventive stent 10. Serpentine bands 12 may be arranged adjacent to one another along the longitudinal axis of the stent 10. Adjacent serpentine bands 12 may be connected to one another by at least one permanent connector strut 20.

The restraining wire 50 may have a distal end 52 and a proximal end 54. Desirably, the proximal end 54 of the wire 50 will extend beyond the longitudinal bounds of the stent 10. The restraining wire 50 may be woven between the cells 34 of the substantially cylindrical framework 26 and about portions of the serpentine bands 12 or connector struts 20. The distal end 52 of the wire 50 may terminate within the bounds of the stent 10 or may extend beyond the bounds of the stent 10.

In some embodiments, the stent 10 may be disposed about a delivery catheter 40. Desirably, the proximal end 54 of the wire 50 will extend beyond the bounds of the stent 10, along the length of the catheter 40 to the catheter proximal end 42. The wire 50 may extend within a lumen of the catheter 40.

Desirably, a restraining wire 50 will be arranged in communication with the stent 10 such that a tensile force upon the wire 50 may constrain the stent 10 from expansion, and in some cases may reduce the diameter of the stent 10. In the case of a self-expanding stent 10, the self-expanding force of the stent 10 to return to a shape-memory configuration may place a tensile load upon the wire 50 or portions of the wire 50 at any time before the stent 10 reaches the shape-memory configuration, or full deployment diameter.

Applying a concentrated force P to the proximal end 54 of the wire 50 in a tension creating direction, such as by pulling on the wire, may directly control expansion or contraction of the stent 10. When the applied load P is less than the amount necessary to overcome the self-expansion force of the stent 10, the stent 10 is allowed to expand in proportion to the magnitude of the applied force P. When the applied load P is greater than the amount necessary to overcome the self-expansion force of the stent 10, the stent 10 is forced to a reduced diameter in proportion to the magnitude of the applied force P. When the applied load P is removed, the stent 10 is allowed to expand to a full deployment diameter.

A repositionable stent 10 having a retaining wire 50 may be placed upon a catheter 40 and delivered to a deployment location within a bodily lumen. If a delivery sheath is utilized to retain the stent 10 in an unexpanded configuration upon the catheter 40, the sheath may be removed when the stent arrives at the deployment location while a force P may be applied to the retaining wire 50. The force P upon the wire 50 may be gradually reduced, allowing the stent 10 to partially self-expand. If it becomes desirable to reposition the stent 10, the force P applied to the retaining wire 50 may be increased, thereby reducing the diameter of the stent 10 and allowing for repositioning. The force P upon the wire 50 may again be reduced, allowing the stent 10 to self-expand further. When the stent 10 is positioned in a final deployment location, the force P may be removed from the wire 50, allowing full expansion of the stent 10.

A retaining wire 50 may be woven between the cells 34 of the stent 10 to traverse any path capable of reducing the diameter of the stent 10 as desired upon the application of an appropriate applied force P upon the wire 50. In some embodiments, a wire 50 may only contact each serpentine band 12 once. In some embodiments, a wire 50 may contact each peak 14 or each straight portion 18 of a serpentine band 12.

In some embodiments, a wire 50 may be wrapped about a stent 10 without passing through any cells 34 of the substantially cylindrical framework 26.

In some embodiments, the distal end 52 of the wire 50 may terminate within the bounds of the stent 10. Desirably, when the distal end 52 of the wire 50 terminates within the bounds of the stent 10, the wire 50 is woven such that friction between the wire 50 and the stent 10 will prevent a portion of the wire 50 from slipping in relation to the stent 10 during expansion of the stent 10. Desirably, the wire 50 is woven such that a lack of friction between the wire 50 and the stent 10 will release the wire 50 from the stent 10 only upon full deployment of the stent 10. Thus, frictional forces may act to hold the wire 50 in communication with the stent 10 until the full deployment diameter is reached, wherein the magnitude of frictional forces drops to a point that friction no longer holds the wire 50 in communication with the stent 10, and a force P applied to the proximal end 54 of the wire 50 will cause the wire to be removed from the stent 10.

In some embodiments, the distal end 52 of a restraining wire 50 may be coupled to a stent 50 or a catheter 40.

In some embodiments, the distal end 52 of the wire 50 may be coupled to a stent 10, a catheter 40 or another portion of the wire 50. In such embodiments, the coupling may be relied upon to secure the wire 50 to the stent 10 during and after stent 10 expansion. The coupling may be designed to detach upon a predetermined condition using any of the detachment methods described herein, such as by the application of a predetermined tensile stress, a predetermined impulse loading or by other known methods, such as bio-absorption or electrolytic detachment as described herein.

In some embodiments, the distal end 52 of the restraining wire 50 may be coupled to a stent 50 or a catheter 40, and the restraining wire 50 may further include a detachment area or necked portion. The detachment area or necked portion may be located proximal to the distal end 52 of the wire 50. The detachment area or necked portion may be designed to detach upon a predetermined condition using any of the detachment methods described herein. For example, a necked portion may sever upon a predetermined impulse loading. A detachment area may be arranged to electrolytically detach upon the application of a predetermined electrical current. Upon detachment, the portion of the restraining wire 50 proximal to the detachment area or necked portion may be removed from the bodily lumen. In some embodiments, a portion of the restraining wire 50 distal to the detachment area or necked portion may remain within the bodily lumen coupled to the stent 10. In some embodiments, a portion of the restraining wire 50 distal to the detachment area or necked portion may remain coupled to the catheter 40, and thus may be removed upon removal of the catheter 40.

In some embodiments, the distal end 52 of the wire 50 may extend beyond the bounds of the stent 10. The distal end 52 of the wire 50 may extend along the length of the catheter 40 to the catheter proximal end 42. Thus, in some embodiments, both the proximal end 54 and the distal end 52 of the wire 50 may extend out of the body. In such embodiments, frictional forces between the wire 50 and the stent 10 need not be relied upon to secure the wire 50 to the stent 10. Manipulation of the expansion of the stent 10 may be accomplished by applying forces P to both the proximal end 54 and distal end 52 of the wire 50. Upon proper placement and expansion of the stent 10 to a full deployment diameter, the wire 50 may be removed by placing a force P upon only one end of the wire 50, thereby extracting the wire 50.

Figure 16:
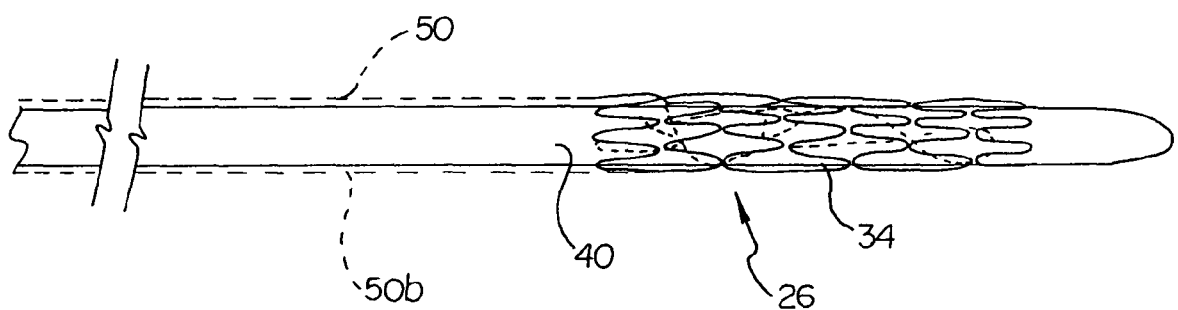
FIG. 16 shows another embodiment of an inventive stent having multiple restraining wires.

In some embodiments, a plurality of wires may be used. Referring to FIG. 16, a first wire 50 and a second wire 50b may be utilized. Desirably, the wires 50, 50b may be arranged to first contact the stent 10 near the midpoint of the stent 10 body, with each wire 50, 50b extending toward an opposite end of the stent 10. Thus, forces P applied to the wires 50, 50b may be distributed more uniformly along the body of the stent 10.

Figure 17:
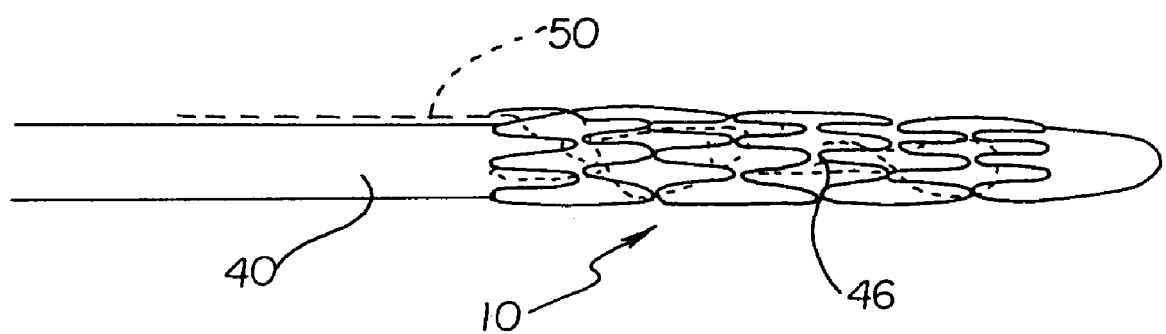
FIG. 17 shows another embodiment of an inventive stent having a restraining wire and a catheter having an engagement portion.

Referring to FIG. 17, in some embodiments, a stent 10 may be disposed about a delivery catheter 40, and a restraining wire 50 may be arranged to slidably engage the catheter at a connecting point 46. A connecting point 46 may be placed anywhere along the length of the catheter 40. Desirably, a connecting point 46 may be positioned near a midpoint of a stent 10 that overlays the catheter 40. A connecting point 46 may help to prevent the stent 10 from translocating proximally or distally along the length of a catheter 40 during expansion or contraction of the stent 10. Upon full deployment of the stent 10, the wire 50 may be removed from the connecting point 46 by applying a force to the proximal end 54 of the wire 50, thereby removing the wire 50 from the stent 10 and the connecting point 46.

A constraining wire 50 may be constructed of any material capable of retaining a stent 10 in a reduced profile state, but which is flexible enough to change shape upon expansion of the stent 10 and be readily withdrawn from the stent 10 and from a bodily lumen. Optionally, to facilitate retraction of the wire 50 from the stent 10, the wire 50 may be constructed from a shape memory material such as nitinol and/or a shape memory polymer. Some examples of suitable shape memory polymers include but are not limited to: acrylate-based polymers, polyurethane-based polymers, polylactide-based polymers and polynorbornene based polymers.

The use of a shape memory material in a restraining wire 50 may provide the wire 50 with the capability to vary the amount of restricting force applied to the stent 10 when the shape memory property is activated by a change in temperature, or pH in the wire 50 or surrounding area. In some embodiments, shape memory activation may be used to detach a coupling or release the restraining wire 50 from the stent 10. The shape memory material may be temperature activated by the heat of the body or heat may be delivered to the wire 50. Alternatively, when the wire 50 is located within a catheter 40 lumen, a warm saline bolus may be injected into the catheter 40 lumen to increase the temperature of the wire 50 prior to or during retraction. In one embodiment of the invention, wherein the shape memory material of the wire 50 is pH activated, a bolus of pH-buffered saline may be injected into a catheter 40 lumen to change the pH of the area surrounding wire 50.

A constraining wire 50 may include a coating. A coating may affect the frictional properties of the wire 50, thereby increasing or decreasing the amount of friction generated between the stent 10 and the wire 50. In some embodiments, coatings such as parylene, urethane, HDPE, Pebax®, silicon, hydrophobic coatings, hydrophilic coatings such as Hydropass™ and Bioslide™, Teflon®, available from DuPont, and/or combinations thereof may be used.

A constraining wire 50 may comprise a solid wire, a wound wire, a braided wire or any other configuration arranged to properly constrain a stent 10. A braided wire 50 may more flexible than a solid wire of similar diameter, and thus may be better suited to withstand multiple shape changes, such as bending.

In another embodiment, a delivery system may include a first sheath arranged to constrain a stent to a partially expanded configuration and a second sheath arranged to constrain a stent to an unexpanded or delivery configuration.

Figure 18:
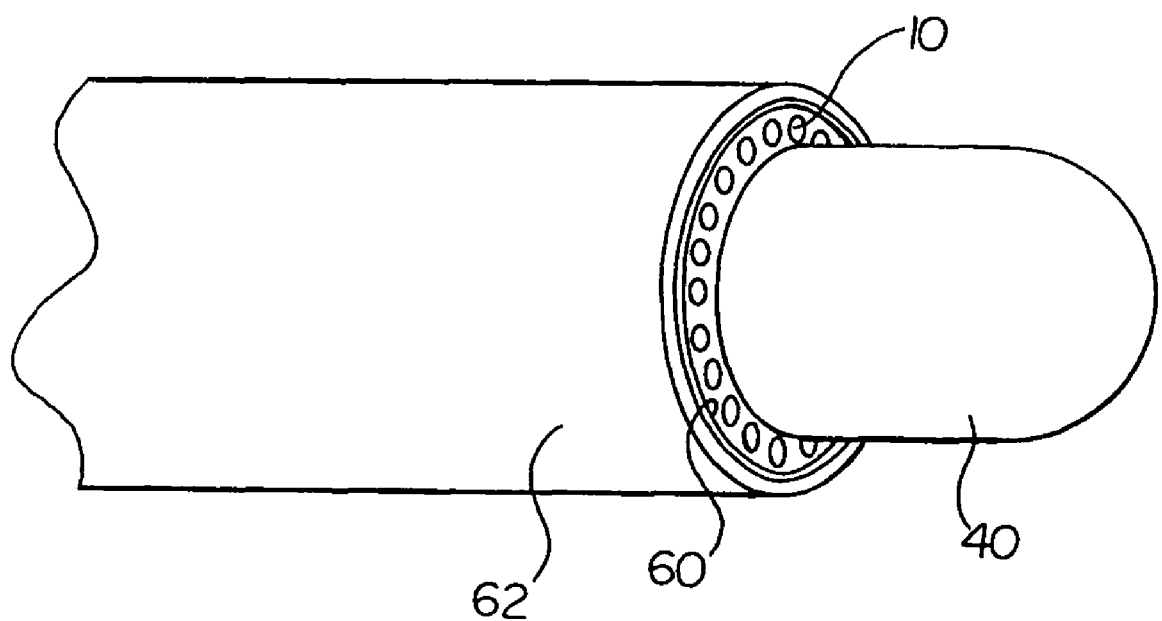
FIG. 18 shows an embodiment of an inventive medical device having an implantable medical device, an inner sheath and an outer sheath.

Referring to FIG. 18, a stent 10 is shown mounted upon a delivery catheter 40. A first or inner sheath 60 is arranged about at least a portion of the stent 10. In some embodiments, the inner sheath 60 may be substantially coextensive with the stent 10. In some embodiments, the inner sheath 60 may extend beyond one or both ends of the stent 10. A second or outer sheath 62 is arranged about at least a portion of the inner sheath 60, and about at least a portion of the stent 10. Desirably, the maximum diameter of the outer sheath 62 is less than the maximum diameter of the inner sheath 60. In some embodiments, the outer sheath 62 may comprise a catheter outer shaft. During delivery of the stent 10, the outer sheath 62 maintains the stent 10 in an unexpanded delivery configuration.

Figure 19:
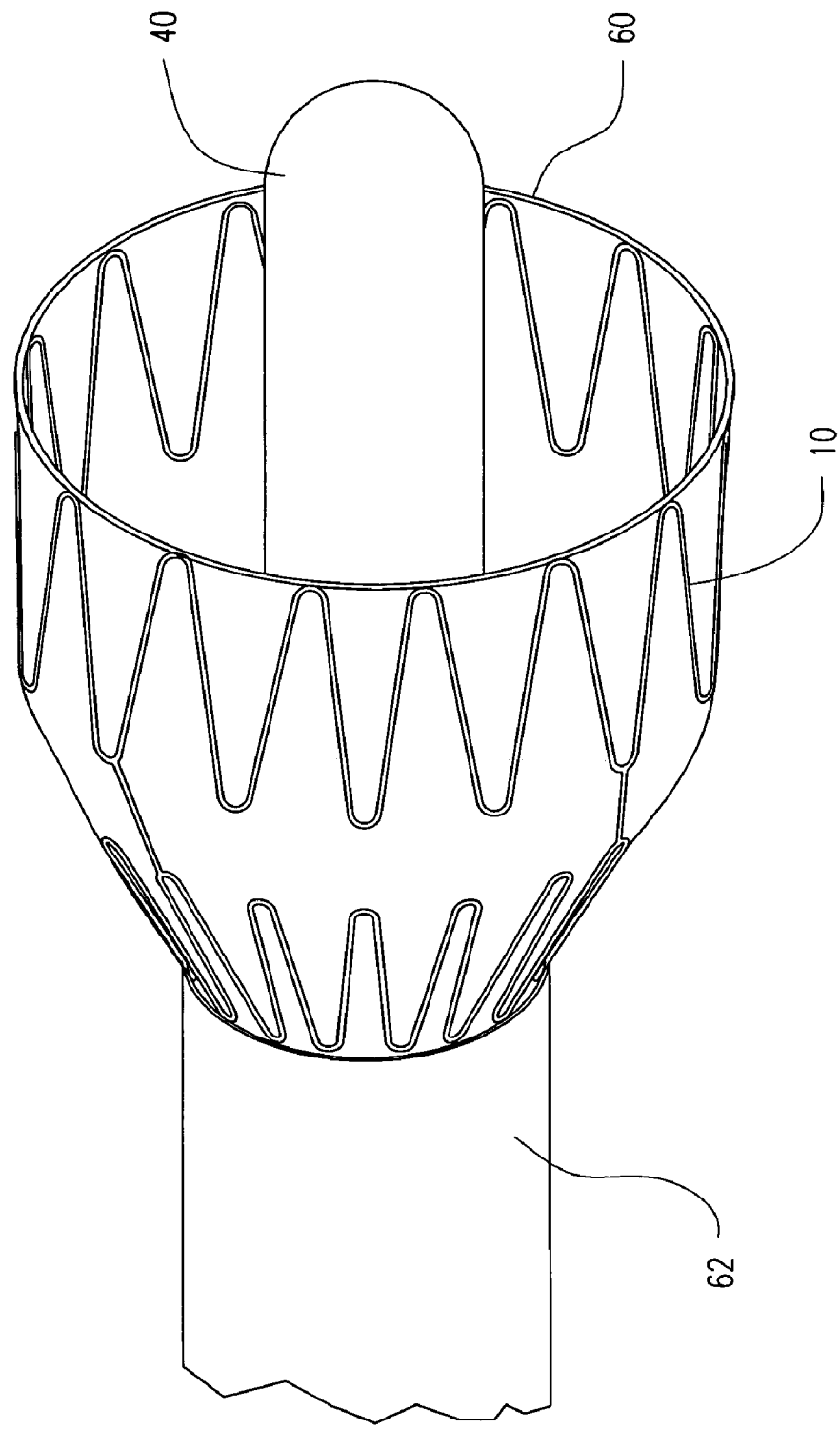
FIG. 19 shows an embodiment of an inventive medical device having a portion of the device partially deployed.

FIG. 19 depicts a partially deployed stent 10 according to an embodiment of the invention. When the stent 10 arrives at the deployment location, the outer sheath 62 may be retracted. As the outer sheath 62 retracts, the stent 10 may self-expand until it becomes constrained by the inner sheath 60.

Desirably, the inner sheath 60 has a maximum diameter that is both larger then the maximum diameter of the outer sheath 60 and smaller than the diameter of the stent 10 when fully deployed. Thus, the inner sheath 60 may maintain the stent 10 at an intermediate deployment diameter. For example, in some embodiments, the maximum diameter of the inner sheath 60 may range from 20% to over 99% of the diameter of the stent 10 when fully deployed. Desirably, the maximum diameter of the inner sheath 60 may range from 50% to 80% of the diameter of the stent 10 when fully deployed.

Desirably, the inner sheath 60 will allow the stent 10 to be repositioned within a bodily lumen after the outer sheath 62 is removed. In some embodiments, the inner sheath 60 may constrain the stent 10 in a partially expanded configuration such that the stent 10 may be moved proximally or distally within the bodily lumen in the partially expanded configuration.

In some embodiments, the inner sheath 60 may allow the stent 10 to be resheathed within the outer sheath 62.

Figure 20:
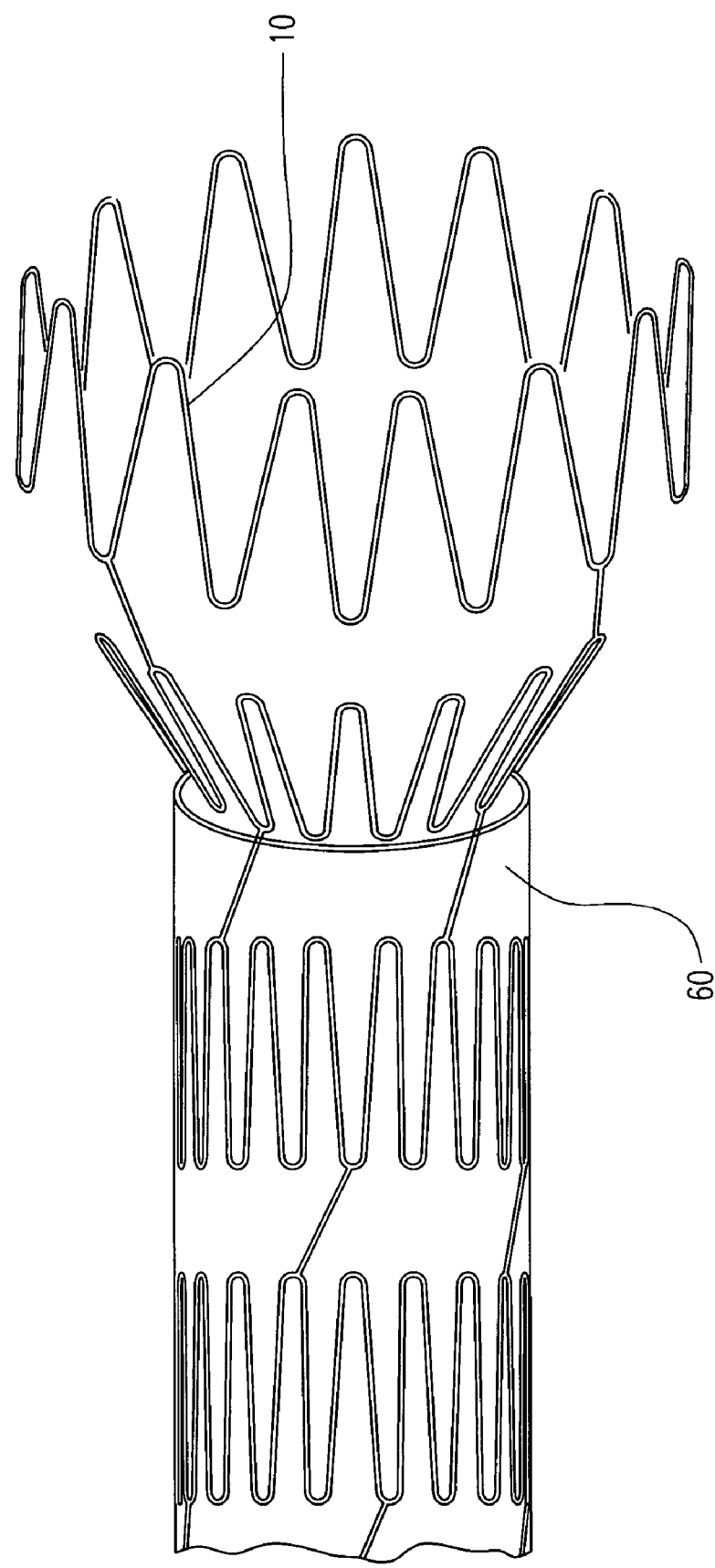
FIG. 20 shows an embodiment of an inventive medical device having a portion of the device fully unsheathed.

As shown in FIG. 20, removal of the inner sheath 60 will allow a self-expanding stent 10 to reach a full deployment diameter.

In some embodiments, the outer sheath 62 may be coupled to the inner sheath 60. Desirably, the outer sheath 62 may be completely retracted from the stent 10 before retraction of the inner sheath 60 begins. Thus, after the outer sheath 62 is removed, continuing to draw the outer sheath 62 away from the stent 10 may in turn remove the inner sheath 60 from the stent 10.

Figure 21:
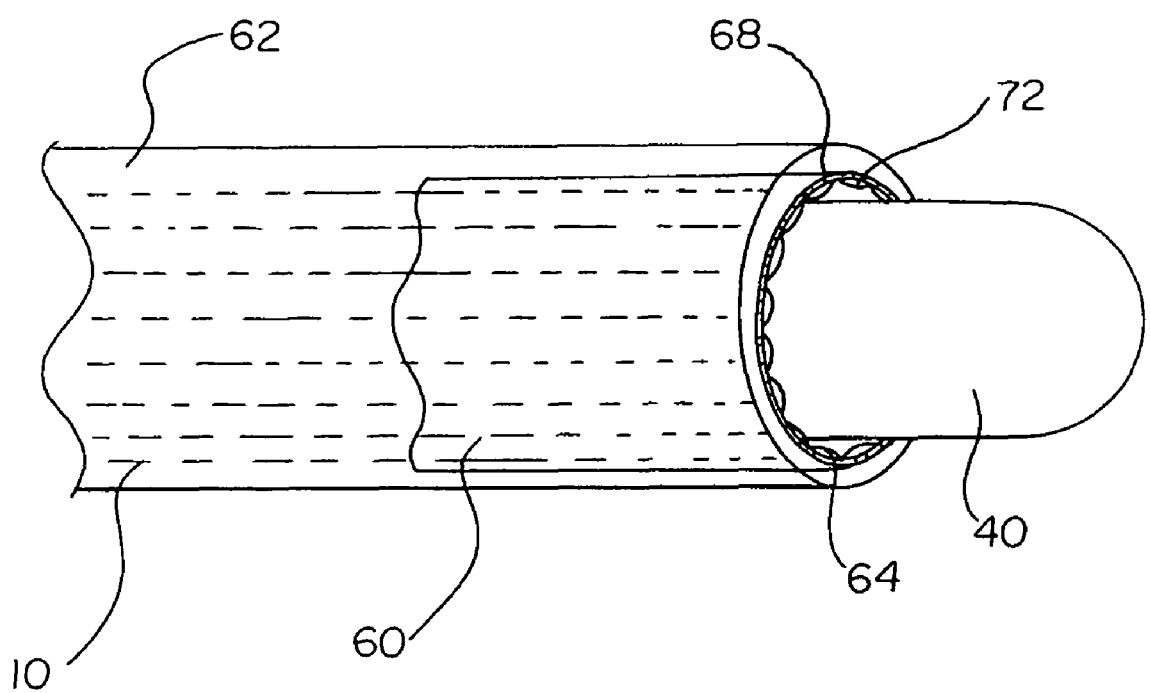
FIG. 21 shows another embodiment of an inventive medical device having an implantable medical device, an inner sheath and an outer sheath.
Figure 22:
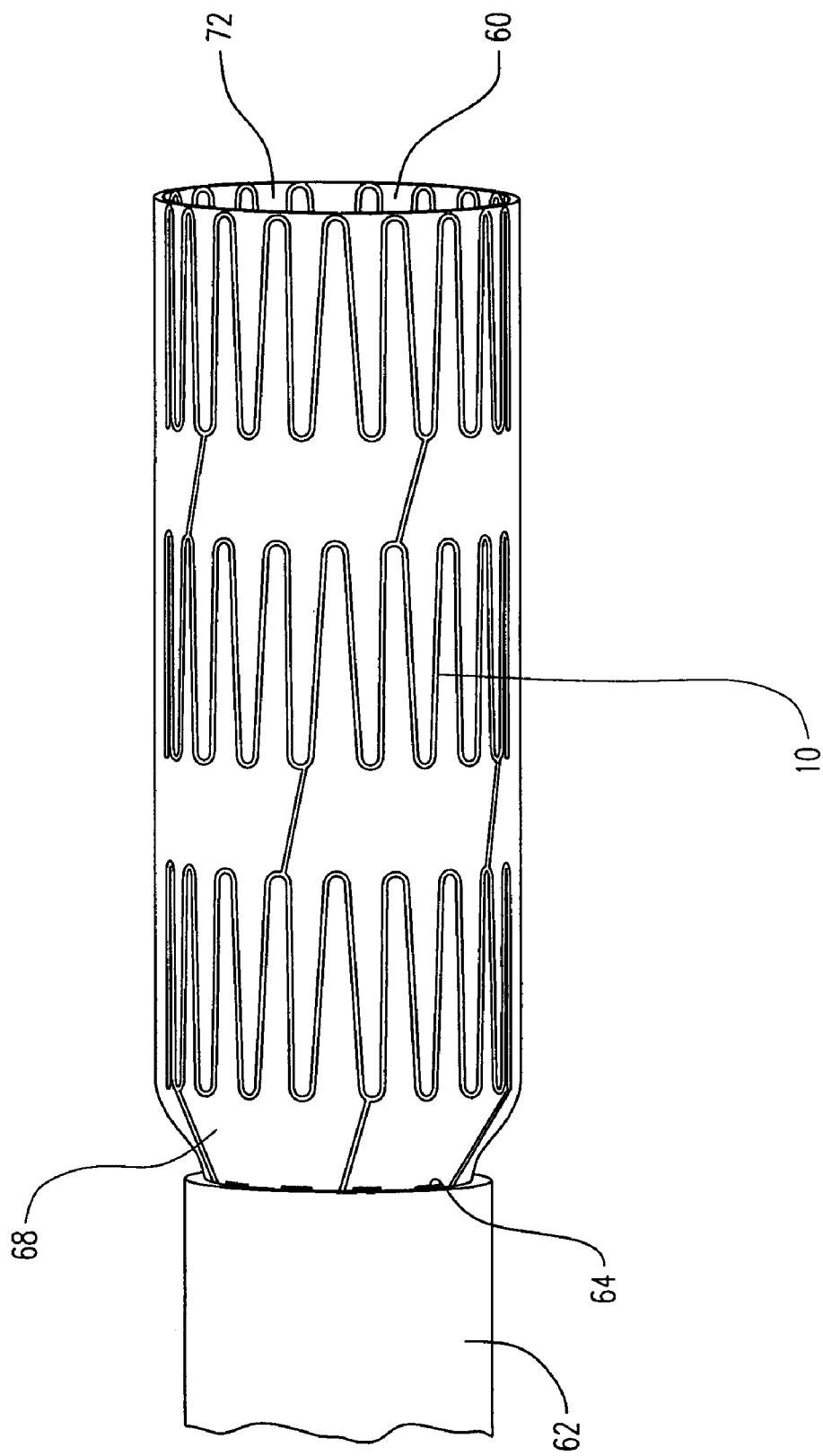
FIG. 22 shows an embodiment of an inventive medical device having an implantable medical device, an inner sheath and an outer sheath, wherein the outer sheath has been retracted.

As shown in FIGS. 21 and 22, in some embodiments, the inner sheath 60 may be coupled to the outer sheath 62 at an attachment point 64 or a plurality of attachment points 64. The attachment point 64 may be located near the distal end of the outer sheath 62.

In some embodiments, a portion of the inner sheath 60 may be folded over another portion of the inner sheath 60 beneath the outer sheath 62. An inner sheath 60 may have a total length similar to the length of a stent 10. The distal end 72 of the inner sheath 60 may be positioned over the distal end of a stent 10. The proximal end 68 of the inner sheath 60 may be coupled to the distal end of the outer sheath 62. When the outer sheath 62 is placed over the stent 10, a portion of the inner sheath 60 may be folded over another portion of the inner sheath 60, and the proximal end 68 and distal end 72 of the inner sheath 60 may be located near the stent 10 distal end. Upon retraction of the outer sheath 62, the inner sheath 60 may unfold, such that the proximal end 68 of the inner sheath 60 may translocate toward the proximal end of the stent 10, while the distal end 72 of the inner sheath 60 may remain near the distal end of the stent 10.

In some embodiments, the inner sheath 60 may be twice as long as a stent 10, such that when a portion of the inner sheath 60 is folded over itself, the inner sheath 60 completely covers the stent 10.

Desirably, a lubricious coating may be included between the inner sheath 60 and the outer sheath 62. A lubricious coating may help prevent binding of the inner sheath 60 with the outer sheath 62 and premature removal of the inner sheath 60. A lubricious coating may further be used between the stent 10 and the inner sheath 60. A lubricious coating between the inner sheath 60 and outer sheath 62 may or may not be the same material as a lubricious coating between the inner sheath 60 and the stent 10.

A lubricious coating may comprise any suitable substance including hydrophobic substances, such as silicone, glycerine or olive oil, and hydrophilic substances, such as polyethylene oxides, optionally linked to the substrate surface by urethane or ureido linkages or interpolymerized with poly(meth)acrylate polymers or copolymers; copolymers of maleic anhydride; (meth)acryl amide polymers and copolymers; (meth)acrylic acid copolymers; poly(vinyl pyrrolidone) and blends or interpolymers with polyurethanes; and polysaccharides.

A lubricious coating may further comprise natural water soluble or water sensitive polymers such as carboxymethyl cellulose, methyl cellulose, hydroxyethyl cellulose and hydroxypropyl cellulose, heparin, dextran, modified dextran and chondroitin sulphate; synthetic water soluble or water sensitive polymers including the polyalkylene glycols and polyoxyalkylene glycols such as polyethylene oxide, polyethylene oxide/polypropylene oxide copolymers and methoxypolyethylene oxide; copolymers of maleic anhydride including methyl vinyl ether-maleic anhydride copolymers; pyrrolidones including poly(vinylpyrrolidone); acryl amides including poly(N-alkylacrylamide); poly(acrylic acid); poly(carboxylic acids); poly(vinyl alcohol); poly(ethyleneimine); polyamides; water soluble nylons; polyurethanes; and the like; and less water soluble or even insoluble derivatives including esterified polymers, salts, amides, anhydrides, halides, ethers, hydrolyzates, acetals, formals, alkylols, quaternary polymers, diazos, hydrazides, sulfonates, nitrates, and ion complexes which are obtained by condensation, addition, substitution, oxidation, or reduction reactions of the above-mentioned water soluble polymers. Further, polymers may be crosslinked with substances having more than one reactive functional group such as diazonium, azide, isocyanate, acid chloride, acid anhydride, imino carbonate, amino, carboxyl, epoxy, hydroxyl, and aldehyde groups.

An outer sheath 62 may be made from any suitable material. An inner sheath 60 may be made from any suitable material, and is desirably flexible. An inner sheath 60 may be made from the same materials as an outer sheath 62, or may be made from different materials. In some embodiments, the inner sheath 60 may comprise a polymer wrapping being made from polymers such as polyolefin, nylon 12 or other desirably thin and strong polymers.

Additional materials which may be used in an inner sheath 60 or an outer sheath 62 include, but are not limited to, polymeric materials including Selar® resins, polyether-polyester block copolymers such as Hytrel® elastomer, Pebax® resins, or other similar extrudable thermoplastics; nylon (polyamide), polyurethane (PU), polyimide (PI), polytetrafluoroethylene (PTFE), expanded polytetrafluoroetylene (ePTFE), polyether ether ketone (PEEK), fluorinated ethylene propylene (FEP), and polybutylene terephthalate (PBT), polyethylene terephthalate, polyvinyl chloride, polyetherurethanes, polyesterurethanes, polyurethane ureas, polyurethane siloxane block copolymers, polyethylene, polypropylene; polyether block amides, such as Pebax® 7033 or 7233; polyester block ethers such as Arnitel® elastomers; polymeric materials, or composites thereof; as well as other thermoplastic elastomers not mentioned.

Additionally, a sheath may be comprised of bio-absorbable materials. The term bio-absorbable as used in this disclosure is synonymous with biodegradable, meaning the ability to be degraded by processes involving biological conditions, such as those present in the bodies of humans or other animals. More specifically, this term indicates the physical or chemical breakdown of the polymer into smaller units which are preferably innocuous, non-toxic and are readily eliminated or metabolized by the body. Some bio-absorbable materials which may be used include polymers, copolymers, block polymers, and mixtures thereof Bio-absorbable polymers and polymer classes include, but are not limited to the following: poly(glycolic acid) (PGA), poly(lactic acid) (PLA), polydioxanes, polyoxalates, poly(.alpha.-esters), polyanhydrides, polyacetates, polycaprolactones, poly(orthoesters), polyamino acids, polyurethanes, polycarbonates, polyiminocarbonates, polyamides, poly(alkyl cyanoacrylates), and mixtures and copolymers thereof. Additional useful polymers include, stereopolymers of L- and D-lactic acid, copolymers of bis(p-carboxyphenoxy) proprionic acid and sebacic acid, sebacic acid copolymers, copolymers of caprolactone, poly (lactic acid)/poly(glycoclic acid)/polyethyleneglycol copolymers, copolymers of polyurethane and poly(lactic acid), copolymers of .alpha.-amino acids, copolymers of .alpha.-amino acids and caproic acid, copolymers of .alpha.-benzyl glutamate and polyethylene glycol, copolymers of succinate and poly(glycols), polyphosphazene, polyhydroxy-alkanoates and mixtures thereof. Binary and ternary systems are contemplated.

Figure 23:
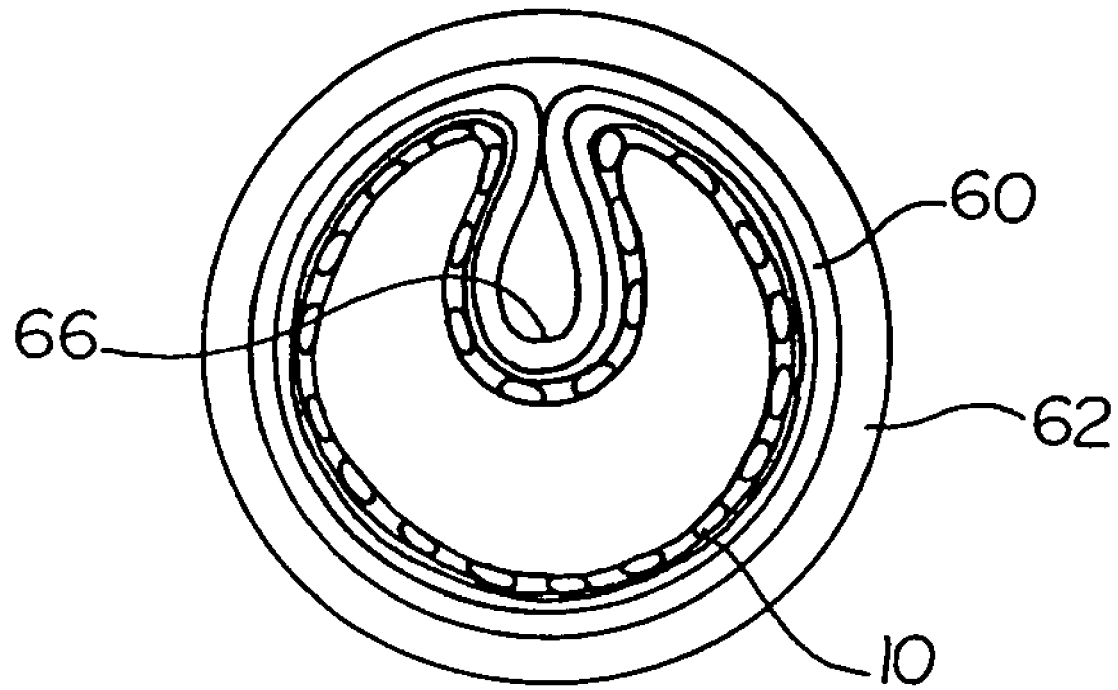
FIG. 23 shows another embodiment of an inventive medical device having an implantable medical device, an inner sheath and an outer sheath.
Figure 24:
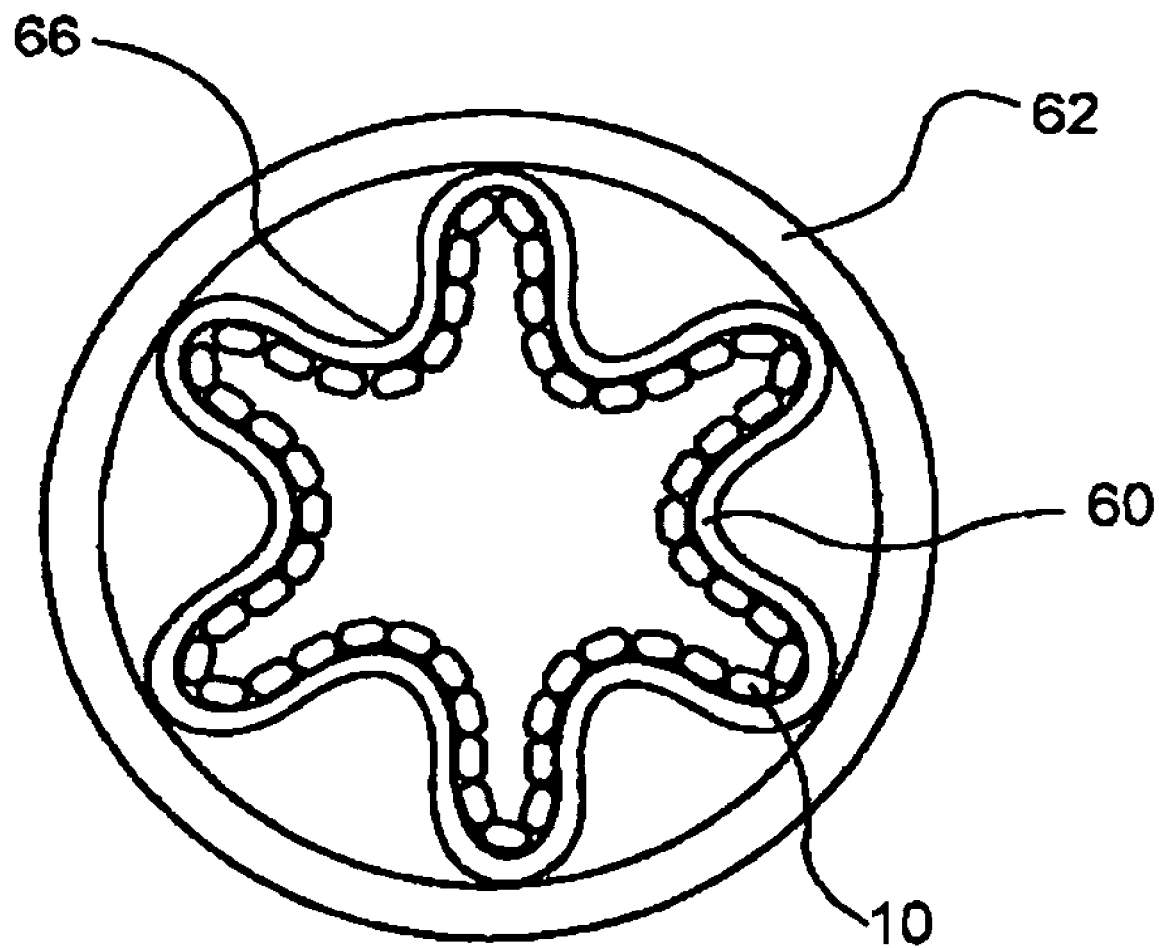
FIG. 24 shows another embodiment of an inventive medical device having an implantable medical device, an inner sheath and an outer sheath.
Figure 25:
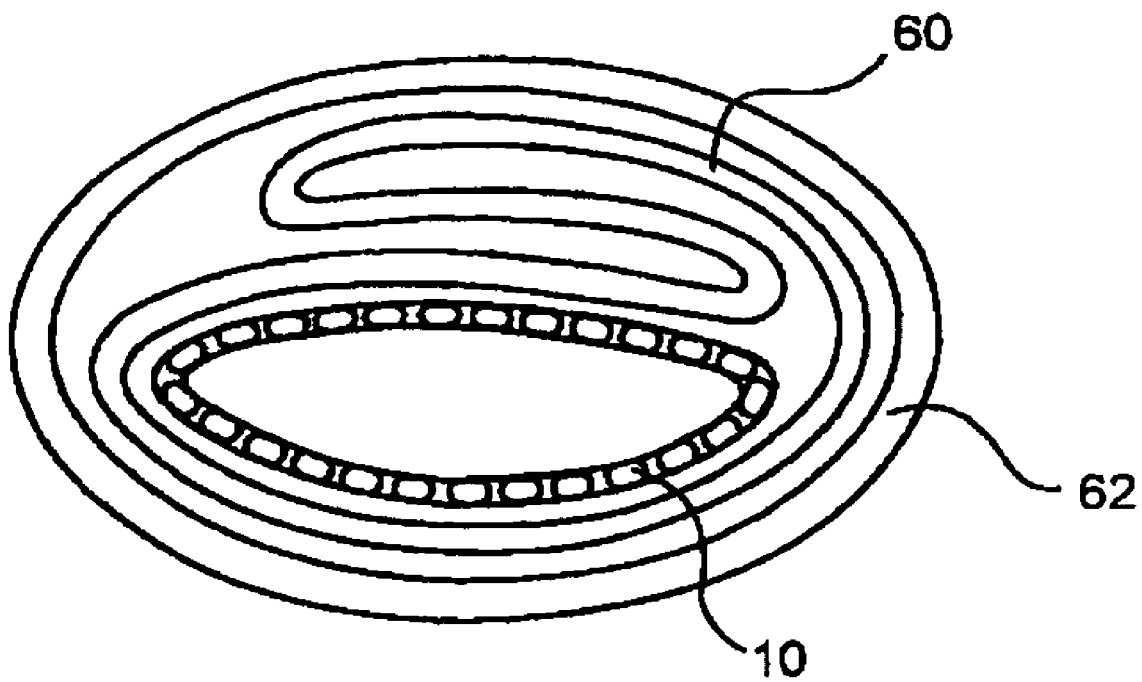
FIG. 25 shows another embodiment of an inventive medical device having an implantable medical device, an inner sheath and an outer sheath.
Figure 26:
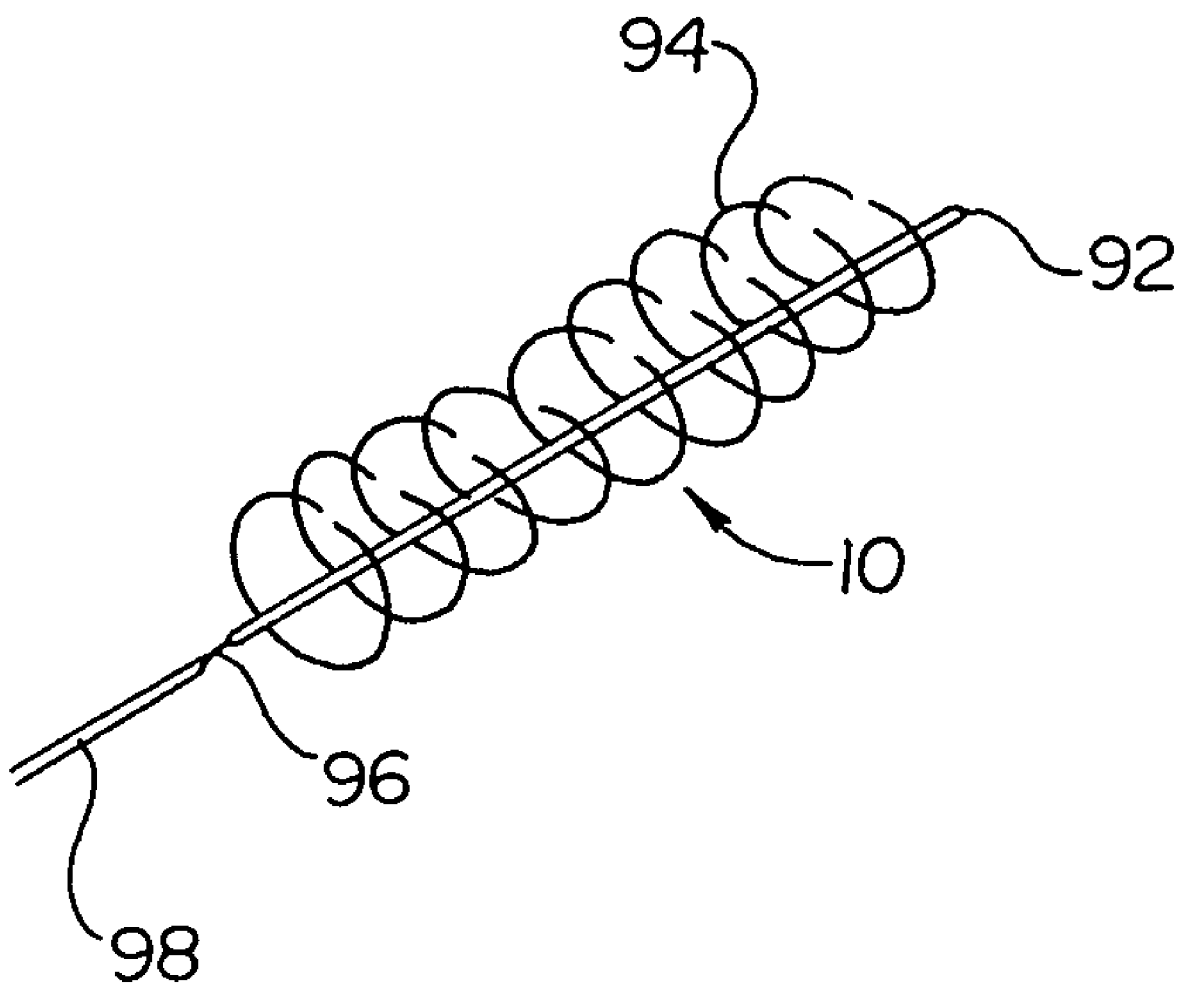
FIG. 26 shows an embodiment of an inventive stent having ribs and an electrolytic detachment area.

FIGS. 23-25 depict further embodiments of an inventive stent delivery system. In some embodiments, the delivery system may comprise a first or inner sheath 60, a second or outer sheath 62 and a stent 10. An inner sheath 60 may be formed from a rolled polymer sheet having a portion of the sheet bonded to another portion. Desirably, a bond 66 may be placed at an edge portion, or may be placed such that two edge portions are bonded together.

Generally, a stent 10 may be placed within an inner sheath 60. The inner sheath 60 and stent 10 may be reduced in diameter and inserted into an outer sheath 62. In a reduced configuration, an inner sheath 60 may have bends or folds. Portions of an inner sheath 60 may be folded over other portions of the inner sheath 60, as shown in FIG. 25. A stent 10 contained within a reduced inner sheath 60 may be cooperatively shaped with respect to the inner sheath, as shown in FIGS. 23 and 24, or may not, as shown in FIG. 25.

An outer sheath 62 may be more rigid than an inner sheath 60. An outer sheath 62 may comprise any desirable appropriate shape, including a circular or ovular cross-section.

In another embodiment, a repositionable stent 10 may comprise a ribbed stent as shown in FIGS. 26-29. A stent 10 may include a backbone 92, a plurality of ribs 94 and a detachment area 96.

A backbone 92 desirably runs the length of the stent 10 and is arranged to support a plurality of ribs 94. A backbone 92 may be straight, curved or may even spiral along the length of the stent 10. Desirably, a backbone 92 may be flexible and able to traverse a tortuous anatomy, yet resilient and capable of returning to an original shape. A backbone 92 may be made from any suitable materials, including polymeric materials, metals, ceramics and composites. In some embodiments, a backbone 92 may comprise a shape memory material such as Nitinol.

The ribs 94 of an inventive stent 10 may be coupled to a backbone 92 and arranged to extend circumferentially or helically. Ribs 94 may extend orthogonally from a backbone 92, or may extend at various other angles to the backbone 92.

Desirably, ribs 94 may be made from a shape memory material, such as one or more biocompatible polymers and/or one or more metals. For example, ribs 94 may be formed from Nitinol, 316L stainless steel, a cobalt chromium alloy such as elgiloy or MP35N, shape memory polymers and/or combinations thereof. Ribs 94 may be arranged to "remember" a shape such that the stent 10 normally takes an expanded configuration. In an expanded configuration, the ribs 94 may desirably support a vessel wall.

The ribs 94 may be coupled to a backbone 92 at an end. The ribs 94 may also be coupled to the backbone 92 at any point along their length. For example, a rib 94 may be coupled to a backbone 92 at a midpoint, and thus a first side of the rib 94 may extend from the backbone 92 in a first circumferential or helical direction, and the second side of the rib 94 may extend from the backbone 92 in a second circumferential or helical direction. Desirably, a coupling between a rib 94 and a backbone 92 comprises a rigid connection. Methods of attachment may include adhesives, laser welding techniques, other welding or brazing techniques, swaging and the like. In some embodiments the backbone 92 and ribs 94 may be integrally formed from a single piece of material, such as by laser cutting a tube of material.

Figure 27:
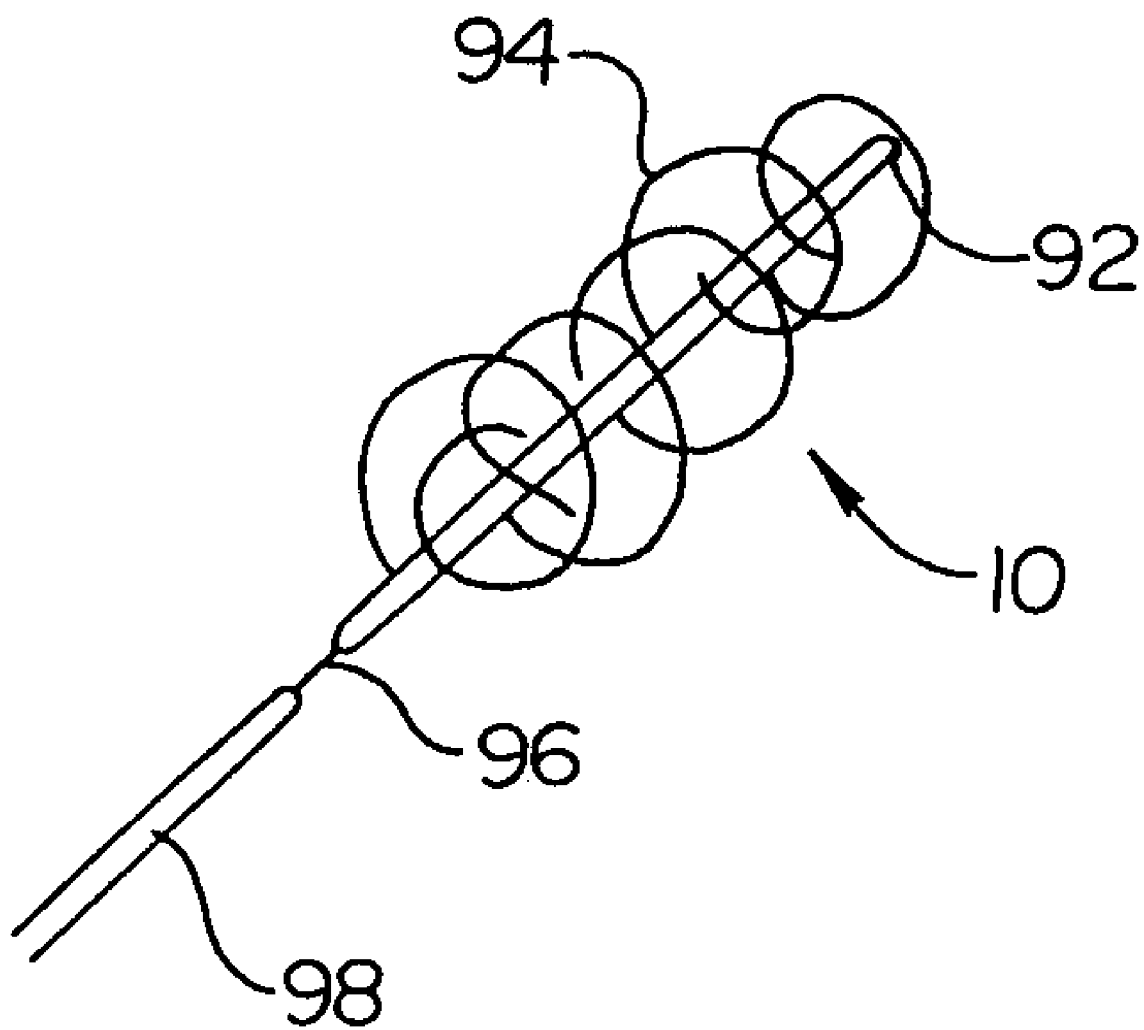
FIG. 27 shows another embodiment of an inventive stent having ribs and an electrolytic detachment area.

Ribs 94 may be of any suitable length. Ribs 94 may extend from the backbone and traverse the stent 10 any rotational amount, including a full 360°. Desirably, ribs 94 may extend at least 120° to 180° about the stent 10. In some embodiments, a rib 94 may extend more than 360°, as shown in FIG. 27. Longer ribs 94 may wrap around the stent 10 and overlap the backbone 92. A rib 94 may overlap a backbone 92 on either side of the backbone 92.

Figure 28:
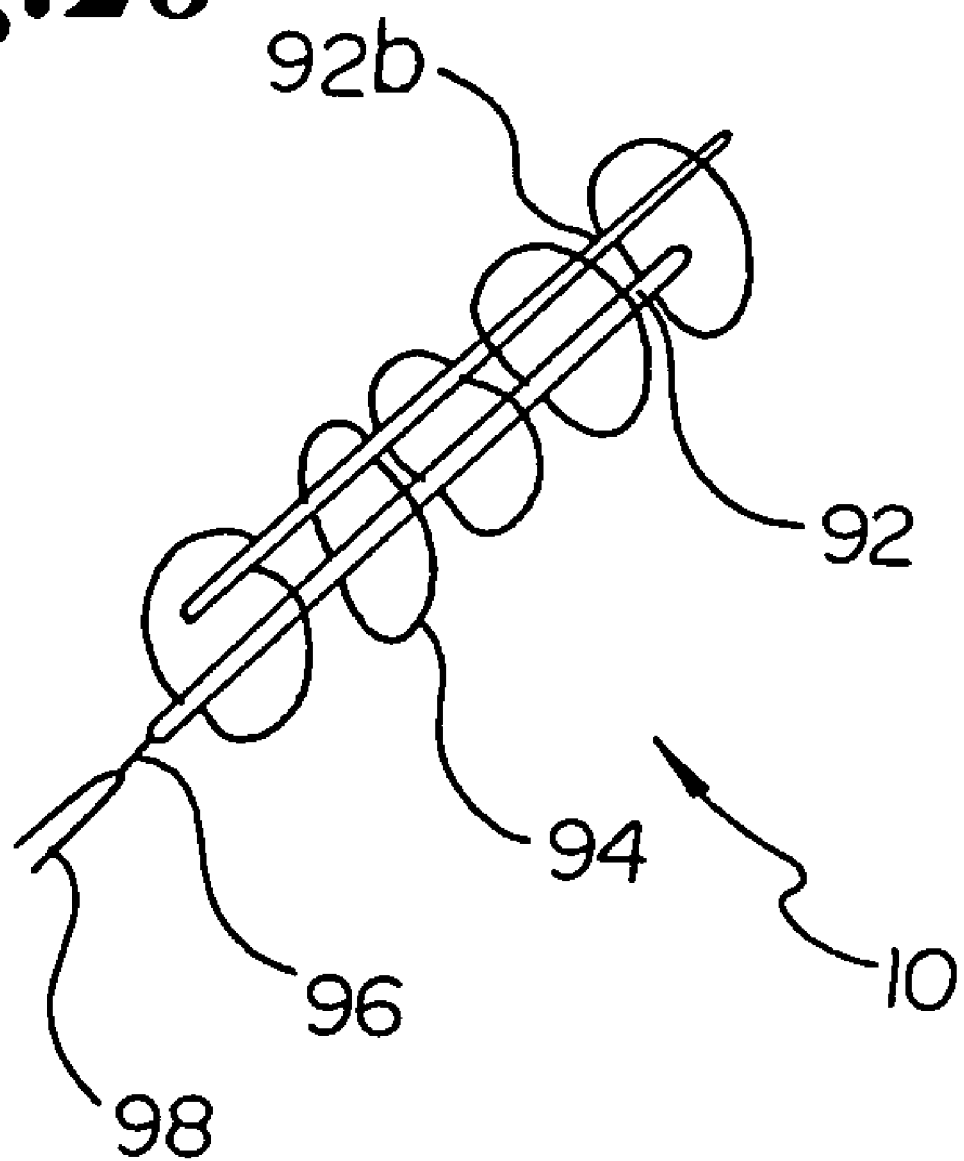
FIG. 28 shows another embodiment of an inventive stent having ribs and an electrolytic detachment area.

In some embodiments, a stent 10 may further comprise a second backbone 92b, as shown in FIG. 28. A second backbone 92b is desirably spaced about the circumference of the stent 10 from the first backbone 92. For example, the first backbone 92 and the second backbone 92b may be 180° apart from one another. A plurality of ribs 94 may generally be coupled to a first backbone 92 or a second backbone 92b. Desirably, at least one rib 94 is coupled to both the first backbone 92 and the second backbone 92b. In some embodiments, every rib 94 may be coupled to both the first backbone 92 and the second backbone 92b.

A stent 10 may be attached to a delivery shaft 98 for delivery to a deployment location. Desirably, the stent 10 will be attached to the delivery shaft 98 at a detachment area 96. Desirably, a backbone 92 of the stent 10 may include or may be coupled to a detachment area 96.

A detachment area 96 desirably has a smaller cross-sectional area than a backbone 92 or a delivery shaft 98. A detachment area 96 may be arranged for electrolytic detachment. Generally, an electrical current may flow through the detachment area 96 and be dispersed into a bodily fluid such as blood contained within a bodily lumen. As the current flows, portions of the detachment area 96 may experience electrolytic corrosion, as previously described herein.

In some embodiments, detachment may occur when electrolytic corrosion has penetrated a full cross-section of a portion of a detachment area 96. In some embodiments, a detachment area 96 may act as a fusible element and melt at a predetermined current level.

In some embodiments, a detachment area 96 may have a higher corrosion potential than the remainder of stent 10. Thus, if current reaches other portions of the stent 10, the detachment area 96 will corrode faster than the remainder of the stent 10. Desirably, the detachment area 96 will achieve detachment before a noticeable corrosion of other portions of the stent 10.

Any suitable material may be selected for a detachment area 96. Materials utilized for a detachment area 96 may include but are not necessarily limited to magnesium, zinc, aluminum, mild steel, low alloy steel, and/or iron.

Figure 29:
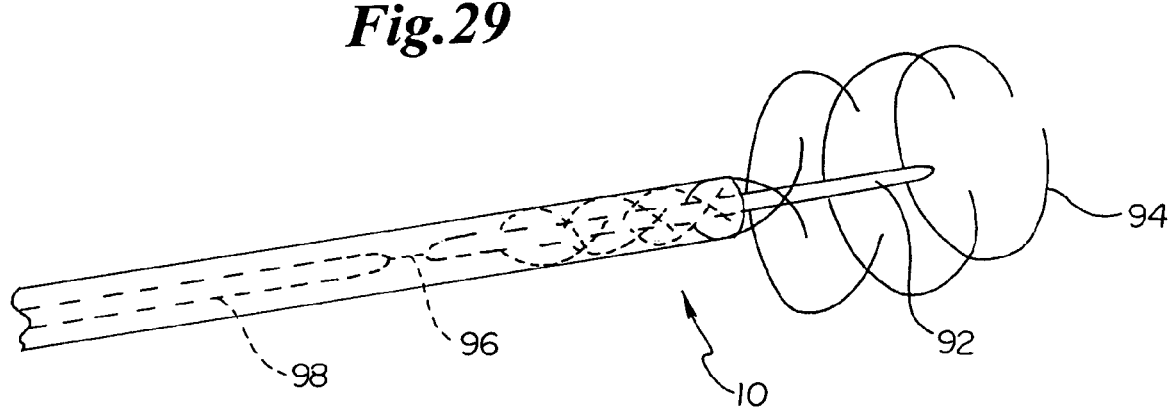
FIG. 29 shows an embodiment of a partially sheathed inventive stent having ribs and an electrolytic detachment area.

An inventive ribbed stent 10 may be delivered to a deployment location within a bodily lumen in a reduced state. FIG. 29 shows a partially unsheathed inventive stent 10. A sheath 97 may contain the stent 10 in a reduced configuration. Desirably, as the stent 10 is placed within a sheath 97, the ribs 94 will bend and lay in a more longitudinal configuration.

The exact configuration of the ribs 94 within the sheath 97 may depend on the shape and size of the sheath 97. A sheath 97 may have an inner lumen that is larger in diameter than the backbone 92 of the stent 10 and smaller than the diameter of the stent 10 when fully expanded. Desirably, a sheath 97 may be as small as possible while still containing the backbone 92 and ribs 94. In some embodiments using a small diameter sheath 97, the ribs 94 may lie flat against the backbone 92 in a longitudinal direction. If a stent 10 includes a first backbone 92 and a second backbone 92*b*, the diameter of a sheath 97 may be increased.

As a sheath 97 is removed from the stent 10, the unsheathed ribs 94 will return to a normal shape-memory expanded configuration. Desirably, the stent 10 may be unsheathed at a deployment location, and the ribs 94 may expand to contact and support a vessel wall. If repositioning of the stent 10 is desired, the stent 10 may be resheathed, and placement may be adjusted.

When the stent 10 is fully unsheathed and positioned in a final deployment location, the stent 10 may be detached from the delivery shaft 98 by electrolytic detachment.

Figure 30:
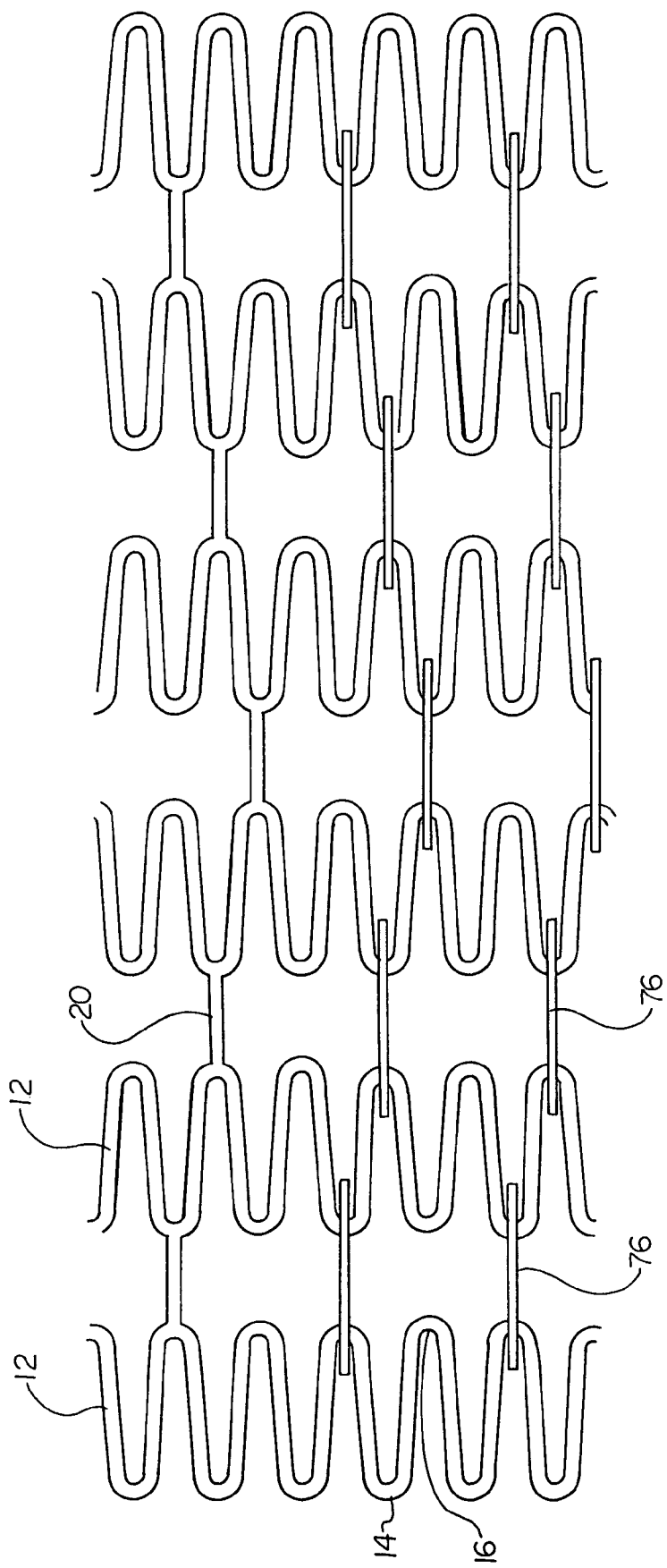
FIG. 30 shows an embodiment of an inventive stent having floating connector struts.

Referring to FIG. 30, in some embodiments, a repositionable stent 10 may comprise a plurality of serpentine bands 12, at least one permanent connector strut 20 connecting adjacent serpentine bands 12, and at least one floating connector strut 76. A floating connector strut 76 may comprise a force transmitting element capable of transmitting selected forces between adjacent serpentine bands 12. Desirably, a floating connector strut 76 may transmit a constraining or diameter-reducing force from a first serpentine band 12 to an adjacent serpentine band 12. Further, a floating connector strut 76 may prevent portions of adjacent serpentine bands 12 from moving more than a predetermined distance away from one another.

A floating connector strut 76 may overlap a first serpentine band 12, extend distal to the first serpentine band 12 and overlap an adjacent serpentine band 12. The floating connector strut 76 may overlap a valley 16 of the first serpentine band 12 and a peak 14 of the adjacent serpentine band 12.

In some embodiments, a floating connector strut 76 may interact with the adjacent serpentine band 12 by transmitting a constraining force from the first serpentine band 12 to the adjacent serpentine band 12, such as a force in a radial direction toward the center of the stent 10. A floating connector strut 76 may be arranged to allow adjacent serpentine bands 12 to move proximally or distally with respect to one another along the longitudinal axis of the stent 10.

Floating connector struts 76 may include any cross-sectional shape. For example, the cross-section may be circular, rectangular, trapezoidal, ovular, or any other suitable shape. Floating connector struts 76 may be made from any suitable material, such as the materials discussed herein.

Floating connector struts 76 may extend parallel to the longitudinal axis of the stent 10, or may extend at an angle. An angle may be desirable, for example, when the peaks 14 and valleys 16 of adjacent serpentine bands 12 are not aligned. Further, a floating connector strut 76 may be straight or may be curved along at least a portion of its length, if not the entirety of its length.

Floating connector struts 76 desirably allow a partially unsheathed self-expanding stent 10 to be resheathed. When a first serpentine band 12 is reduced in diameter, floating connector struts 76 that are coupled to the first band 12 may transmit a constraining force to an adjacent serpentine band 12, thereby reducing the diameter of the adjacent band 12. Thus, a partially unsheathed self-expanding stent 10 having floating connector struts 76 may be resheathed and repositioned within a bodily lumen.

Any number of floating connector struts 76 may be used within a stent 10. Desirably, at least one floating connector strut 76 may be placed between adjacent serpentine bands 12.

Desirably, under normal conditions for a deployed stent 10, a floating connector strut 76 will allow the adjacent serpentine bands 12 to move laterally with respect to one another without interference.

Referring to FIGS. 31 and 32, embodiments of floating connector struts 76 are depicted. A floating connector strut 76 may have a proximal extreme 82 and a distal extreme 83. A floating connector strut 76 may include looped or hooked end portions 78, which may provide for an interior loop 79. The distance between an extreme portion 82, 83 and a hooked end portion 78 may be selected to provide for an interior loop 79 of predetermined dimension. A larger interior loop 79 may allow for a greater range of adjustment in the distance between the first serpentine band 12 and the adjacent serpentine band 12. A floating connector strut 76 may be arranged to cross between the interior and exterior portions of the stent 10, as shown in FIG. 32.

Referring to FIGS. 33 and 34, a floating connector strut 76 may comprise a loop. FIG. 33 depicts an embodiment having an interior portion 104, an exterior portion 106 and connectors 108. The interior portion 104 and exterior portion 106 may overlap adjacent serpentine bands 12. Connectors 108 may connect the interior portion 104 to the exterior portion 106 such that a portion of each of the serpentine bands 12 are within the interior loop 79 formed.

FIG. 34 depicts a one piece floating connector strut 76 comprising a loop. The ends of the floating connector strut 76 loop may be coupled together at a coupling 110. A coupling 110 may comprise any suitable connection, for example, an adhesive connection, a swaged connection, a soldered, welded or brazed connection, and the like. The floating connector strut 76 loop may form an interior loop 79 that may contain a portion of each of the serpentine bands 12 connected by the floating connector strut 76.

The invention is also directed to methods of using the inventive devices described herein.

Any of the inventive stents disclosed herein having disengagable connector struts may be delivered to a deployment location in an unexpanded configuration. The stent may be unsheathed and allowed to expand to an intermediate deployment diameter. Desirably, the disengagable connector struts constrain the stent from further expansion. Desirably, the stent may be repositioned within the bodily lumen at the intermediate deployment diameter. In some embodiments, a partially unsheathed stent may be resheathed if it is desirable to achieve proper placement, as the disengagable connector struts desirably allow a partially unsheathed stent to be resheathed.

When the stent is fully unsheathed and proper placement has been achieved at the intermediate deployment diameter, the disengagable connector struts may be electrolytically disengaged, thereby allowing the stent to expand to a full deployment diameter in the final location.

An inventive stent having cantilevered support members may be delivered to a deployment location in an unexpanded configuration. The stent may be partially unsheathed and a portion of the stent may be allowed to expand. If an adjustment in placement of the stent is desirable, the partially unsheathed stent may be resheathed, as the cantilevered support members desirably allow a partially unsheathed stent to be resheathed. After resheathing, the stent may again be partially unsheathed and a portion of the stent may be allowed to expand. When positioning is proper, the sheath may be removed completely, and the stent may be allowed to expand to a full deployment diameter.

An inventive stent having a retaining wire may be delivered to a deployment location in an unexpanded configuration. Desirably, the retaining wire may be used to control the diameter of the stent. If a sheath is used to restrain the stent during delivery, the sheath may be removed while keeping the retaining wire in tension. The tension on the retaining wire may be reduced allowing the stent to expand. Desirably, tension may be reduced gradually, thus allowing for a gradual expansion of the stent. If repositioning of the stent is desirable, expansion may be stopped by increasing the amount of tension applied to the retaining wire. If reducing the diameter of the stent is desired, the tension applied to the wire may be further increased, causing a reduction in diameter. The stent may be repositioned, and the tension applied to the retaining wire may again be reduced. When proper placement of the stent is achieved, tension on the retaining wire may be released and the stent may be allowed to expand to a full deployment diameter. Desirably, a retaining wire may release from the stent when the tension is released and the stent expands to a predetermined diameter. The retaining wire may then be removed.

An inventive delivery system comprising an inner sheath and an outer sheath may be used to deliver a stent to a deployment location within a bodily lumen. The outer sheath may be retracted. Desirably, the inner sheath will allow the stent to expand to an intermediate deployment diameter. Desirably, the stent may be repositioned within the bodily lumen at the intermediate deployment diameter. When proper positioning of the stent is achieved at the intermediate deployment diameter, the inner sheath may be removed, and the stent may expand to a full deployment diameter.

An inventive stent having ribs, a backbone and a detachment area may be delivered to a deployment location attached to a delivery shaft in an unexpanded configuration while being restrained by a sheath. The stent may be partially or fully unsheathed and a portion of the stent or the entire stent may be allowed to expand to a full deployment diameter. If repositioning of the stent is desirable, the stent may be resheathed and the placement may be adjusted. The stent may then be partially or fully unsheathed.

When the stent is fully unsheathed and proper placement has been achieved, the stent may be electrolytically detached from the delivery shaft.

Any of the inventive stents disclosed herein may have serpentine bands with shapes other than those shown. For example, the peaks within a serpentine band may not all be aligned with one another about the circumference of the stent. Some peaks may extend further in a longitudinal direction that other peaks. Similarly, the valleys within a serpentine band may not all be aligned with one another about the circumference of the stent. Some valleys may extend further in a longitudinal direction that other valleys. Furthermore, the peaks and valleys may also be connected by struts which are not straight. For example, the struts may be curved having one or more bends in them. Also, peaks and valleys within a band may be uniformly spaced from one another or may be non-uniformly spaced from one another.

Any embodiments of the inventive stents disclosed above may be provided with a uniform diameter or may taper in portions or along the entire length of the stent. Also, the width and/or thickness of the various portions of the inventive stents may increase or decrease along a given portion of the stent. For example, the width and/or thickness of the circumferential bands and/or permanent connector struts and disengagable connector struts may increase or decrease along portions of the stent or along the entire length of the stent. The amplitude and wavelength of several successive first circumferential bands may remain constant while the width and/or thickness of the successive first circumferential bands decrease. Similarly, the amplitude and wavelength of several successive second circumferential bands may remain constant while the width and/or thickness of the successive second circumferential bands decrease.

The inventive stents may also be provided with end effects by modifying the stent such that that one or both ends are more rigid or more flexible than the remainder of the stent. Any of the inventive stents disclosed herein may be modified to have proximal-most and/or distal-most circumferential bands of a greater total circumferential length than the remaining circumferential bands. Any of the inventive stents disclosed herein may also be modified to have proximal-most and/or distal-most circumferential bands of a lesser total circumferential length than the remaining circumferential bands. Moreover, any of the inventive stents disclosed herein may also be modified so that one of the ends has circumferential bands of a lesser total circumferential length than the circumferential band of the other end which in turn is longer or shorter than the total length of any of the remaining circumferential bands.

Also, one or both of the end circumferential bands may be modified to be of a greater longitudinal extent than the remaining circumferential bands or to be of a lesser longitudinal extent than the remaining circumferential bands. Each of the two end circumferential bands may differ in longitudinal extent with one another and with the remaining circumferential bands.

The invention also contemplates modifying the ends of any of the inventive stents so that the two proximal-most and/or two distal-most circumferential bands have more connections therebetween than the remaining circumferential bands or fewer connections therebetween than the remaining circumferential bands.

Further, the proximal-most and/or distal-most circumferential bands may be of a greater mass than the remaining bands or a lower mass than the remaining bands. They may be thicker than the remaining bands or thinner than the remaining bands.

It is understood that the above discussed modifications resulting in end effects may be applied to multiple circumferential bands at one or both ends of the stent and are not limited to the proximal-most and distal-most circumferential bands.

The stents disclosed herein may also be modified by employing different types of connections between the circumferential bands. To that end, any of the connectors and connector configurations disclosed herein may be used in any of the disclosed embodiments. Shaped connectors may also be used including connectors that have one or more bends therein. The connectors may extend from peaks to valleys, from peaks to peaks, from valleys to peaks and/or from valleys to valleys.

The connectors may range in width from being wider than the width of the widest serpentine bands in the stent, to being narrower than the narrowest serpentine bands in the stent or anywhere inbetween. Regions of different flexibility in the stent may also be achieved by using wider connectors in some regions, for example on one or both of the ends of the stent, and narrower connectors in the other regions of the stent (e.g. the middle) or vice versa.

The invention also contemplates embodiments in which the spacing between adjacent circumferential bands varies in different portions of the stent. For example, the proximal-most circumferential band and/or the distal-most circumferential band may be spaced further apart from the circumferential bands adjacent thereto or may space closer thereto. This would result in using longer connectors between the end bands or shorter connectors, depending on the configuration. In one embodiment, both the proximal-most and the distal-most circumferential bands are more closely spaced to adjacent circumferential bands than the spacing between the remaining circumferential bands and further, the spacing between the proximal-most circumferential band and the circumferential band adjacent thereto differs from the spacing between the distal-most circumferential band and the circumferential band adjacent thereto.

It is also within the scope of the invention for any of the stents disclosed herein to have connectors extending from regions other than peaks and valleys or corners of peaks and valleys. For example, the connectors may extend from straight portions midway between adjacent peaks and valleys, from straight portions one quarter of the way between peaks and valleys, from straight portions three quarters of the way between peaks and valleys, or anywhere else between peaks and valleys. Further, connectors may extend from anywhere along a peak or a valley.

As shown in the various embodiments, the connectors between circumferential bands may extend in a longitudinal direction or may have first and second ends which are circumferentially and longitudinally offset from one another, such as depicted in FIG. 2. The connectors may also include portions which are non-parallel to the longitudinal axis of the stent.

The 'phase relationship' between adjacent circumferential bands may also be modified in any of the embodiments. For example, peaks of adjacent cylindrical bands may be in longitudinal alignment with one another or may be unaligned with one another in the longitudinal direction. Similarly, peaks on one band may be longitudinally aligned with valleys on an adjacent circumferential band, such as shown in FIG. 1, or may be unaligned with valleys on an adjacent circumferential band. Some of the adjacent circumferential bands may be aligned while other adjacent bands may not be aligned.

The stent patterns disclosed herein may also be used for bifurcated stents. One or more legs and/or the trunk of a bifurcated stent may be provided with any of the stent designs disclosed herein.

The inventive stents may be manufactured using known stent manufacturing techniques. Suitable methods for manufacturing the inventive stents include laser cutting, chemical etching or stamping of a tube. The inventive stents may also be manufactured by laser cutting, chemically etching, stamping a flat sheet, rolling the sheet and, optionally, welding the sheet. Other suitable manufacturing techniques include electrode discharge machining or molding the stent with the desired design. The stent may also be manufactured by welding individual sections, for example, circumferential bands, together. Any other suitable stent manufacturing process may also be used.

Any suitable stent material may be used in the manufacture of the inventive stents. Examples of such materials include polymeric materials, metals, ceramics and composites. Suitable polymeric materials include thermotropic liquid crystal polymers (LCP's). Where the stent is made of metal, the metal may be stainless steel, cobalt chrome alloys such as elgiloy, tantalum or other plastically deformable metals. Other suitable metals include shape-memory metals such as nickel-titanium alloys generically known as "nitinol", platinum/tungsten alloys and titanium alloys.

The invention also contemplates the use of more than one material in the inventive stents. For example, adjacent serpentine bands may be made from different material. Permanent connector struts may be made from different materials than the serpentine bands.

The inventive stents may include suitable radiopaque coatings or other markers for viewing under an imaging device, such as a fluoroscope or an MRI device. For example, the stents may be coated with gold or other noble metals or sputtered with tantalum or other metals. The stents may also be made directly from a radiopaque material to obviate the need for a radiopaque coating or may be made of a material having a radiopaque inner core. Other radiopaque metals which may be used include platinum, platinum-tungsten, palladium, platinum-iridium, rhodium, tantalum, or alloys or composites of these metals.

The inventive stents may also be provided with various bio-compatible coatings to enhance various properties of the stent. For example, the inventive stents may be provided with lubricious coatings. The inventive stents may also be provided with drug-containing coatings which release drugs over time. The increased surface area of a stent having angled or curved connector struts provides for increased drug coatability. The angled or curved struts also provide for point contact with a crimper versus strut/strut contact. Less contact with the crimper results in less disruption of the drug coating.

The inventive stents may also be provided with a sugar or more generally a carbohydrate and/or a gelatin to maintain the stent on a catheter during delivery of the stent to a desired bodily location. Other suitable compounds for treating the stent include biodegradable polymers and polymers which are dissolvable in bodily fluids. Portions of the interior and/or exterior of the stent may be coated or impregnated with the compound. Mechanical retention devices may also be used to maintain the stent on the balloon during delivery. To that end, the use of other coatings on the inventive stents is also within the scope of the invention.

A coating may comprise one or more non-genetic therapeutic agents, genetic materials and cells and combinations thereof as well as other polymeric coatings.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation the family of bone morphogenic proteins ("BMP"s"),BMP-2, BMP-3, BMP-4, BMP-5, BMP-6 (Vgr-1), BMP-7 (OP-1), BMP-8, BMP-9, BMP-10, BMP-1, BMP-12, BMP-13, BMP-14, BMP-15, and BMP-16. Desirable BMP"s are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog"proteins, or the DNA"s encoding them.

Cells can be of human origin (autologous or allogeneic) or from an animal source (xenogeneic), genetically engineered if desired to deliver proteins of interest at the deployment site. The cells may be provided in a delivery media. The delivery media may be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL®), fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

The inventive stents may also be used as the framework for a graft. Suitable coverings include nylon, collagen, PTFE and expanded PTFE, polyethylene terephthalate and KEVLAR, or any of the materials disclosed in U.S. Pat. No. 5,824,046 and U.S. Pat. No. 5,755,770. More generally, any known graft material may be used including synthetic polymers such as polyethylene, polypropylene, polyurethane, polyglycolic acid, polyesters, polyamides, their mixtures, blends and copolymers.

The inventive stents may find use in coronary arteries, renal arteries, peripheral arteries including iliac arteries, arteries of the neck and cerebral arteries. The stents of the present invention, however, are not limited to use in the vascular system and may also be advantageously employed in other body structures, including but not limited to arteries, veins, biliary ducts, urethras, fallopian tubes, bronchial tubes, the trachea, the esophagus, the prostate and the bowels.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent comprising an expandable framework and an electrical lead, the expandable framework comprising:
   a plurality of serpentine bands including a first serpentine band and a second serpentine band, adjacent serpentine bands connected by connector struts, each serpentine band comprising alternating peaks and valleys connected by band struts, the connector struts including permanent connector struts and disengageble connector struts;
   the first serpentine band connected to the second serpentine band by at least one permanent connector strut extending from a valley of the first serpentine band to a peak of the second serpentine band;
   each remaining valley of the first serpentine band connected to a peak of the second serpentine band by a disengagable connector strut;
   wherein said electrical lead extends from said expandable framework and is electrically coupled directly to each of the disengagable connector struts such that the disengagable connector struts disengage by electrolytic detachment.

2. The stent of claim 1, wherein the stent includes more disengagable connector struts than permanent connector struts.

3. The stent of claim 1, further comprising a second electrical lead and at least one other disengagable connector strut, wherein said second electrical lead connects to said other disengagable connector strut.

4. The stent of claim 1, wherein the stent is at least partially self-expanding.

5. The stent of claim 4, wherein the stent self-expands to an intermediate deployment diameter, the stent being restrained from further expansion by at least one disengagable connector strut.

6. The stent of claim 5, wherein the stent self-expands to a full deployment diameter upon disengagement of said at least one disengagable connector strut.

7. The stent of claim 1, wherein at least one disengagable connector strut comprises a necked portion.

8. The stent of claim 7, wherein said disengagement occurs at said necked portion.

9. The stent of claim 7, wherein said at least one disengagable connector strut is connected to a serpentine band at a necked portion.

10. The stent of claim 1, wherein upon disengagement of said at least one disengagable connector strut, said at least one disengagable connector strut no longer transmits forces between said first and second serpentine bands.

11. The stent of claim 1, wherein said stent transitions from a closed cell design to an open cell design upon disengagement of said disengageble connector struts.

12. A stent comprising:
a cylindrical metal framework having a plurality of cells and an electrical lead, said framework comprising a first serpentine band, a second serpentine band, at least one permanent connector strut and a plurality of disengageble connector struts, each serpentine band comprising alternating peaks and valleys connected by band struts, at least one of said permanent connector struts connecting a valley of the first serpentine band to a peak of the second serpentine band, the plurality of disengagable connector struts connecting the remaining valleys of the first serpentine band to the remaining peaks of the second serpentine band, the electrical lead attached to each of said disengagable connector struts; wherein the number of cells decreases upon disengagement of said disengagable connector strut; and wherein the mass of the metal in the metal framework decreases upon disengagement of said disengagable connector strut.

13. The stent of claim 12, wherein the stent is self-expanding and comprises a sheath, the stent capable of being re-sheathed after at least one of the first and second serpentine bands has been fully unsheathed.

14. The stent of claim 13, wherein a portion of each cell is defined by a portion of a permanent connector strut after disengagement of said disengagable connector struts.

15. The stent of claim 12, wherein the stent is at least partially self-expanding.

16. The stent of claim 12, wherein the stent is constructed and arranged such that the disengagable connector strut disengages by electrolytic detachment.

17. The stent of claim 12, comprising more disengagable connector struts than permanent connector struts.

18. The stent of claim 12, wherein at least a portion of a disengagable connector strut is made from a material having a higher corrosion potential than a material used to form said at least one permanent connector strut.

* * * * *